(12) United States Patent
Anderson et al.

(10) Patent No.: US 7,842,029 B2
(45) Date of Patent: Nov. 30, 2010

(54) APPARATUS AND METHOD HAVING A COOLING MATERIAL AND REDUCED PRESSURE TO TREAT BIOLOGICAL EXTERNAL TISSUE

(75) Inventors: Robert S. Anderson, Livermore, CA (US); Alon Maor, Los Altos, CA (US); Steve Young, Discovery Bay, CA (US)

(73) Assignee: Aesthera, Livermore, CA (US)

( * ) Notice: Subject to any disclaimer, the term of this patent is extended or adjusted under 35 U.S.C. 154(b) by 1690 days.

(21) Appl. No.: 11/024,340

(22) Filed: Dec. 27, 2004

(65) Prior Publication Data

US 2005/0251118 A1   Nov. 10, 2005

Related U.S. Application Data

(63) Continuation-in-part of application No. 10/841,273, filed on May 7, 2004.

(51) Int. Cl.
*A61B 18/20* (2006.01)
(52) U.S. Cl. .............. 606/2; 607/88; 607/89; 128/898; 606/10; 606/11; 606/12
(58) Field of Classification Search .............. 606/2–15; 607/88–89; 128/898
See application file for complete search history.

(56) References Cited

U.S. PATENT DOCUMENTS

| | | |
|---|---|---|
| 3,674,031 A | 7/1972 | Weiche |
| 3,712,306 A | 1/1973 | Bryne |

(Continued)

FOREIGN PATENT DOCUMENTS

AU   55604/86   10/1987

(Continued)

OTHER PUBLICATIONS

PCT International Preliminary Report of Patentability and Written Opinion of the International Searching Authority for PCT/US2005/015131, International filing date Apr. 29, 2005, mailing date Nov. 16, 2006, (11 pages).

(Continued)

*Primary Examiner*—Henry M Johnson, III
*Assistant Examiner*—Jeffrey B Lipitz
(74) *Attorney, Agent, or Firm*—Blakely, Sokoloff, Taylor & Zafman LLP

(57) ABSTRACT

Devices and methods having a cooling material and reduced pressures to treat biological external tissue using at least one energy source are disclosed. The cooling material may be water, ethyl alcohol, and/or any other material having a vapor pressure below atmospheric pressure. The energy source may be incoherent light, coherent light, a radio frequency, ultrasound, a laser, and/or any other type of energy that can be applied through the device. The features of various embodiments of the device include the generation of positive pressure and/or negative pressure through one or more pressure conduits, the application of an object within a recess of the device, and measurements through various sensors on the device. These sensors may be monitored and/or controlled through a display element having rows and columns of pixels on the device. The device may be a handheld device or an add-on to existing devices in some embodiments, and may include skin color sensors, temperature sensors, motion sensors, vapor pressure sensors, material sensors, and/or capacitance sensors.

28 Claims, 29 Drawing Sheets

U.S. PATENT DOCUMENTS

| | | | |
|---|---|---|---|
| 3,794,039 A | 2/1974 | Kollner et al. | |
| 3,862,627 A | 1/1975 | Hans, Sr. | |
| 4,388,924 A | 6/1983 | Weissmann et al. | |
| 4,562,838 A | 1/1986 | Walker | |
| 4,573,970 A | 3/1986 | Wagner | |
| 4,600,403 A | 7/1986 | Wagner | |
| 4,742,235 A | 5/1988 | Koji | |
| 5,000,752 A | 3/1991 | Hoskin et al. | |
| 5,057,104 A | 10/1991 | Chess | |
| 5,059,192 A | 10/1991 | Zaias | |
| 5,171,215 A | 12/1992 | Flanagan | |
| 5,226,907 A | 7/1993 | Tankovich | |
| 5,405,368 A | 4/1995 | Eckhouse | |
| 5,441,498 A | 8/1995 | Perkins | |
| 5,519,534 A | 5/1996 | Smith et al. | |
| 5,595,568 A | 1/1997 | Anderson et al. | |
| 5,626,631 A | 5/1997 | Eckhouse | |
| 5,735,844 A | 4/1998 | Anderson et al. | |
| 5,824,023 A | 10/1998 | Anderson | |
| 5,853,407 A * | 12/1998 | Miller | 606/9 |
| 5,964,749 A | 10/1999 | Eckhouse et al. | |
| 6,048,352 A | 4/2000 | Douglas et al. | |
| 6,071,239 A | 6/2000 | Cribbs et al. | |
| 6,162,218 A | 12/2000 | Elbrecht et al. | |
| 6,168,590 B1 | 1/2001 | Neev | |
| 6,187,001 B1 * | 2/2001 | Azar et al. | 606/9 |
| 6,273,884 B1 | 8/2001 | Altshuler et al. | |
| 6,277,116 B1 | 8/2001 | Utely et al. | |
| 6,280,438 B1 | 8/2001 | Eckhouse et al. | |
| 6,315,772 B1 | 11/2001 | Marchitto et al. | |
| 6,387,089 B1 | 5/2002 | Kreindel et al. | |
| 6,387,380 B1 | 5/2002 | Knowlton | |
| 6,438,424 B1 | 8/2002 | Knowlton | |
| 6,461,348 B1 | 10/2002 | Bertan | |
| 6,461,354 B1 | 10/2002 | Olsen et al. | |
| 6,508,813 B1 * | 1/2003 | Altshuler | 606/9 |
| 6,511,475 B1 | 1/2003 | Altshuler et al. | |
| 6,514,243 B1 | 2/2003 | Eckhouse et al. | |
| 6,517,532 B1 | 2/2003 | Altshuler et al. | |
| 6,595,934 B1 | 7/2003 | Hissong et al. | |
| 6,605,080 B1 | 8/2003 | Altshuler et al. | |
| 6,662,054 B2 | 12/2003 | Kreindel et al. | |
| 6,749,624 B2 * | 6/2004 | Knowlton | 607/104 |
| 6,766,202 B2 | 7/2004 | Underwood et al. | |
| 6,835,184 B1 | 12/2004 | Sage et al. | |
| 7,108,689 B2 | 9/2006 | Eckhouse et al. | |
| 7,250,047 B2 | 7/2007 | Anderson et al. | |
| 7,643,883 B2 | 1/2010 | Kreindel | |
| 2001/0025190 A1 | 9/2001 | Weber et al. | |
| 2002/0049483 A1 * | 4/2002 | Knowlton | 607/101 |
| 2002/0169442 A1 | 11/2002 | Neev | |
| 2003/0167032 A1 | 9/2003 | Ignon | |
| 2003/0199859 A1 | 10/2003 | Altshuler et al. | |
| 2004/0082940 A1 * | 4/2004 | Black et al. | 606/9 |
| 2005/0049543 A1 | 3/2005 | Anderson et al. | |
| 2005/0049583 A1 | 3/2005 | Swanson | |
| 2005/0215987 A1 * | 9/2005 | Slatkine | 606/9 |
| 2005/0222555 A1 | 10/2005 | Manstein et al. | |
| 2005/0234527 A1 | 10/2005 | Slatkine | |
| 2005/0251117 A1 | 11/2005 | Anderson | |
| 2005/0251118 A1 | 11/2005 | Anderson | |
| 2006/0058714 A1 | 3/2006 | Rhoades | |
| 2006/0189964 A1 | 8/2006 | Anderson | |
| 2006/0253178 A1 | 11/2006 | Masotti | |
| 2006/0259102 A1 | 11/2006 | Slatkine | |
| 2007/0010861 A1 | 1/2007 | Anderson et al. | |
| 2007/0142885 A1 | 6/2007 | Hantash et al. | |
| 2007/0179482 A1 | 8/2007 | Anderson | |
| 2007/0185432 A1 | 8/2007 | Etheredge, III et al. | |
| 2008/0065176 A1 | 3/2008 | Zhang et al. | |
| 2008/0200910 A1 | 8/2008 | Burger | |
| 2009/0005801 A1 | 1/2009 | Eastman | |

FOREIGN PATENT DOCUMENTS

| | | |
|---|---|---|
| EP | 0784997 | 7/1997 |
| EP | 0806913 | 6/2002 |
| EP | 1338263 | 8/2003 |
| FR | 2667247 | 4/1991 |
| GB | 2378392 | 2/2003 |
| GB | 2369057 | 2/2006 |
| IL | 147009 | 12/2001 |
| IL | 150094 | 6/2002 |
| IL | 160510 | 2/2004 |
| WO | WO-86/01728 | 3/1986 |
| WO | WO 96/23447 | 8/1996 |
| WO | WO 02/094116 A1 | 11/2002 |
| WO | WO 02094116 A | 11/2002 |
| WO | WO 03/049633 | 6/2003 |
| WO | WO-03/079916 | 10/2003 |
| WO | WO 03/096919 A1 | 11/2003 |
| WO | WO 2004/007022 A1 | 1/2004 |
| WO | WO 2004007022 A | 1/2004 |
| WO | WO 2004/037068 A1 | 5/2004 |
| WO | WO 2004037068 A | 5/2004 |
| WO | WO 2005/082435 | 9/2005 |
| WO | WO-2006/012752 | 2/2006 |
| WO | WO-2006/031632 | 3/2006 |
| WO | PCT/IL2006/000897 | 8/2006 |
| WO | WO-2006/093384 | 9/2006 |
| WO | WO 2006/122136 | 11/2006 |
| WO | WO 2007/015247 | 2/2007 |

OTHER PUBLICATIONS

PCT International Preliminary Report of Patentability and Written Opinion of the International Searching Authority for PCT/US2005/015126, International filing date Apr. 29, 2005, mailing date Nov. 16, 2006, (12 pages).

PCT Search Report and Written Opinion for PCT International Appln No. PCT/US2005/015131, mailed Dec. 20, 2005. (18 pages).

Derwent Publication Ltd, London GB; AN 2005-804121 XP002414902 & JP 2005 334188 A (Eiburu KK) Dec. 8, 2005 Abstract (1 page).

Fay, et al. *Three Approaches for Estimating The Elastic Modulus of the Tympanic Membrane*, Journal of Biomechanics 38 (2005) pp. 1807-1815 (9 pages).

Goh, et al. *Stress Transfer in Collagen Fibrils Reinforcing Connective Tissues: Effects of Collagen Fibril Slenderness and Relative Stiffness*, The Journal of Theoretical Biology, vol. 245 (2007) pp. 305-311 (7 pages).

PCT Notification of Transmittal of The International Search Report and The Written Opinion of the International Searching Authority or the Declaration; the PCT International Search Report and Written Opinion for PCT International Appln No. PCT/US2006/017948, mailed Oct. 25, 2007. (19 pages).

PCT Written Opinion of the International Searching Authority for PCT International Appln No. PCT/US2006/017948, mailed May 27, 2008. (13 pages).

Sasaki, et al. *Stress-Strain Curve and Young's Modulus of a Collagen Molecule as Determined by the X-Ray Diffraction Technique*, J. Biomechanix, vol. 29, No. (5 pages).

Yang, et al. *Micromechanical Bending of Single Collagen Fibrils Using Atomic Force Microscopy*, 2007 Wiley Periodicals, Published online Jan. 31, 2007 in Wiley InterScience (www.interscience.wiley.com) DOI: 10.1002/jbm.a.31127, pp. 160-168 (9 pages).

PCT International Search Report and PCT Written Opinion for PCT International Appln No. US2005/015126, mailed Jul. 26, 2005 (18 pages).

L.L. Polla, et al. "Melanosomes are a primary target of Q-switched ruby laser irradiation in guinea pig skin", *Journal of Investigative Dermatology*, 89, pp. 281-286, 1987.

"PCT International Preliminary Report on Patentability", PCT/US2008/004101, mailed Oct. 15, 2009, 9 pages.

"PCT International Search Report and Written Opinion", PCT/US2006/017948, (Nov. 29, 2007), 11 pages.

"PCT International Search Report and Written Opinion", PCT/US2008/004101, (Dec. 3, 2008), 17 pages.

"PCT Invitation to Pay Additional Fees", PCT/US2005/015131, (Aug. 5, 2005), 8 pages.

"PCT Invitation to Pay Additional Fees", PCT/US2008/004101, (Aug. 12, 2008), 5 pages.

"PCT Invitation to Pay Additional Fees", PCT/US2006/017948, (Jun. 18, 2007), 6 pages.

\* cited by examiner

Time at temperature to burn biological external tissue (e.g., skin).

APPARATUS AND METHOD HAVING A COOLING MATERIAL AND REDUCED PRESSURE TO TREAT BIOLOGICAL EXTERNAL TISSUE

RELATED APPLICATIONS

The present application is a Continuation-In-Part to U.S. patent application Ser. No. 10/841,273, filed on May 7, 2004.

FIELD OF THE INVENTION

The present invention relates to methods and devices useful in modification, treatment, destruction, and/or removal of tissue.

BACKGROUND OF THE INVENTION

Devices utilized in dermatological treatments often incorporate light based energy sources or high frequency rf electrical energy sources. Examples of such devices are described in U.S. Pat. No. 6,511,475. Some devices include both technologies.

A. Lasers and Light-Based Technologies

Lasers and light-based devices have been used for many years in the treatment of dermatological conditions. Soon after the laser was invented in 1957, medical researchers started to explore its use for a wide range of dermatological procedures. In recent years, especially since the mid-90's, the technology has been commercialized into numerous different devices that remove unwanted hair, wrinkles, fine lines and various facial blemishes ("skin rejuvenation"), tattoos, and vascular and pigmented lesions. Because of the short treatment time, virtually no patient "down-time" and fewer side effects, several of these laser- or light-based treatments have become more widely used than the conventional alternatives.

Light energy, when applied directly to the human body, is absorbed by the target chromophore; by the hemoglobin in the blood; the water in the skin; the melanin in the skin; and/or by the melanin in the hair follicles, depending on the wavelength(s) of the light used. Lasers generating different wavelengths of light were found early on to have different properties, each being preferable for specific procedures. In addition to lasers that emit a coherent, monochromatic light, several manufacturers have also introduced devices that emit light of a wide range of wavelengths that practitioners then filter to select the appropriate wavelength for a specific treatment. These "multi-wavelength" or "multi-application" light-based devices have the advantage of performing several different aesthetic treatments, and thus costing the practitioner less than purchasing several lasers individually.

FIG. 1a is a diagram showing the various layers of the skin and potential targets for photo therapy and/or electrical therapy. When light energy first impacts the skin, it encounters the epidermis, the outer most layer of skin. One of the substances that comprise the epidermis is melanin, the brown pigmentation that most of us have in our skin. Darker individuals have more melanin than lighter ones. For very dark individuals, melanin may comprise more than 20% of the epidermis. For light skin individuals, melanin may comprise only 1 to 2% of the epidermis.

Melanocytes in the upper epidermis generate this melanin in response to sunlight. The melanin migrates from the cell and forms a protective umbrella over the fibroblasts and other cells in the skin. The melanin absorbs harmful UVA and UVB radiation that can cause cell damage. It also absorbs visible light, absorbing blue light more than red light.

The epidermis is very thin as it is only 50 to 100 microns in thickness. Consequently, despite the strong absorption by melanin, a reasonable percentage of the light passes through the epidermis into the upper layer of the dermis. For a fair skin person, as little as 15% of the light in the visible portion of the spectrum is absorbed in the epidermis. For a darker person, the percentage absorbed can be more than 50%.

After passing through the epidermis, the light impacts a region called the dermal plexus. This is a thin region at the outer most region of the dermis. It contains a high concentration of small capillary vessels that provide nourishment to the overlying epidermis. The blood in these vessels absorbs between 35% and 40% of the visible portion of the light that impacted the skin.

Clearly for a moderate to dark skin individual, the majority of the visible portion of the spectrum is absorbed in the epidermis and the dermal plexus. Very little energy remains to treat a target located deeper than the dermal plexus.

FIG. 1b shows the percentage of incident energy transmitted, as a function of wavelength, through the epidermis for three different skin types. The figure shows a low percentage of the incident energy in the visible portion of the spectrum is transmitted through the epidermis. The energy not transmitted is absorbed, resulting in a rise in temperature of the epidermis and possibly resulting in the burning of the tissue.

FIG. 1c shows the percentage of incident energy transmitted through the dermal plexus for two different levels of blood concentration (shown as ratios of blood to the rest of the tissue in a given volume). As in the epidermis, the energy not transmitted is absorbed and can produce burning. More importantly, the energy absorbed in the dermal plexus is not available to heat a target such as collagen or tattoo ink that is located beneath the dermal plexus. By reducing the concentration in half, the energy transmitted is doubled.

B. High Frequency rf Electrical Devices

In addition to light based therapies, high frequency rf electrical energy is also becoming common in devices used to treat wrinkles, unwanted hair and unwanted vascular lesions. One of the basic principles of electricity is an electric current passing through a resistive element generates heat in that element. The power dissipated in the element is proportional to the square of the electrical current and also proportional to the resistance of the element. The heat generated is the product of the power times the length of time the power is being dissipated.

A second basic principle of electricity is the electric current seeks the path of least resistance. If two or more such paths exist, the current divides itself proportionally to the resistance of each path. For example, if two such paths exist and one path is twice the resistance of the other, twice the current will pass through the path with the lesser resistance than passes through the path with more resistance. The distribution of power and energy is also in the ratio of the resistances. In the current example, two times the power is dissipated in the lower resistance path than in the higher path. The path with the lesser resistance will heat at twice the rate as the higher resistance path.

High frequency rf energy in dermatology works on the principles described above. In this case, the various tissues and components of the body are the electrical resistors. As the rf current passes through these tissues, energy is dissipated and the temperature of the tissue rises. If the tissue is a blood vessel, it may reach a temperature at which the blood denatures and coagulates. If the tissue is collagen, it may reach a temperature at which the collagen denatures and is destroyed. The body's natural immune system removes the destroyed tissue, starting a process to regenerate new tissue.

The electrical resistance of various tissues varies widely. Tissues in the body with relatively high resistance are bone, fat and the outer layer of the epidermis. Tissues with moderate resistance are connective tissue and the dermis. The tissue with the lowest resistance is the blood. When high frequency electricity is used in dermatological applications, it tends to follow the pathways of the blood vessels, avoiding the fatty tissues and connective tissues.

SUMMARY OF THE DESCRIPTION

There are many different embodiments of apparatuses and methods which are described below. The apparatuses are typically (but not necessarily) handheld devices which apply energy (e.g., coherent and/or incoherent light) from one or more sources in the handheld device. The device may include a negative pressure conduit (e.g., a tube which couples the skin to a vacuum source/pump) which can be used to draw the skin into a region of the device. This will tend to stretch the skin and bring one or more targets (below the surface of the skin) closer to the surface so that these targets receive more incident energy as a result of being closer to the surface.

The device may also include a pixilated display for displaying information (e.g., skin temperature, elapsed treatment time, etc.). The device may also include sensors (e.g., skin color sensors, temperature sensors, motion sensors, vapor pressure sensors, material sensors, and/or capacitance sensors), and may also include an object which is used to mechanically push the skin (thereby providing a positive pressure to a portion of the skin). A device may have multiple, different sources of energy. The sources of energy may, for example, be different laser diodes which emit light of different wavelengths. A device may include a pressure conduit which creates a positive pressure (e.g., a pressure above ambient atmospheric pressure). This pressure conduit may, in certain embodiments, be the same conduit which provides a vacuum or it may be a different, separate conduit.

It will be appreciated that there are various alternative apparatuses which can have various combinations of the different features. For example, a handheld device may include the following features and/or a subset of these features: a negative pressure conduit (e.g., a tube coupled to a vacuum pump to generate a vacuum over a treatment area); a positive pressure conduit (e.g., a tube coupled to an air pump to allow the device to be released after a treatment and/or to "float" over the skin as the device is moved into a position over the skin); and an object to mechanically push the skin (e.g., a piston and/or plunger to push blood away from a treatment area just before exposing the area to energy); and multiple, different sources of energy (e.g., several light sources of different wavelengths and/or other properties); and one or more sensors (e.g., one or more skin color sensors and/or skin temperature sensors to provide feedback to a user, and/or to an automatically controlled processing system before, during, and/or after a treatment; and a pixilated display having rows and columns of pixels on a portion of the device (e.g., a backlit liquid crystal display device which displays skin temperature and other information); and two different vacuum regions, a first vacuum region creating a vacuum in a border region of external biological tissue which surrounds a desired treatment area of external biological tissue and a second vacuum region which applies a vacuum to the desired treatment area after a vacuum has been applied to the border region; and other aspects and/or features described herein.

In one aspect a device includes a cavity which, when pressed against a biological external tissue forms a chamber against (or emncompassing) the biological external tissue. In one aspect, a device may include a material in the chamber to vaporize at the pressure below atmospheric pressure to prevent burning the biological external tissue. The material may be water, ethyl alcohol, and/or any material that has a vapor pressure below atmospheric pressure.

Various methods of operating these apparatuses are also described. In one aspect, a method to treat a target includes furnishing a material (e.g., a liquid) to a biological external tissue inside an inner chamber, applying an energy to the biological external tissue inside the inner chamber, and causing the material to evaporate. In one aspect the material evaporates during application of the energy to treat the target. In one aspect, an outer portion of a device and an inner chamber of the device are applied to the biological external tissue such that the outer portion contacts the biological external tissue and the inner chamber occupies a space above a portion of the biological external tissue having the target. In one aspect, pressure within the inner chamber may be reduced to a first pressure that is below atmospheric pressure to bring at least some of the biological external tissue into the inner chamber and to also cause the material to evaporate, thereby providing evaporative cooling which may occur before, during or after the application of the energy to treat the target. In another aspect, the biological external tissue that is outside the device may be prevented from stretching. Other exemplary aspects are also described.

BRIEF DESCRIPTION OF THE DRAWINGS

The present invention is illustrated by way of example and not limitation in the Figures of the accompanying drawings in which like references indicate similar elements.

DETAILED DESCRIPTION

Figure 2A:
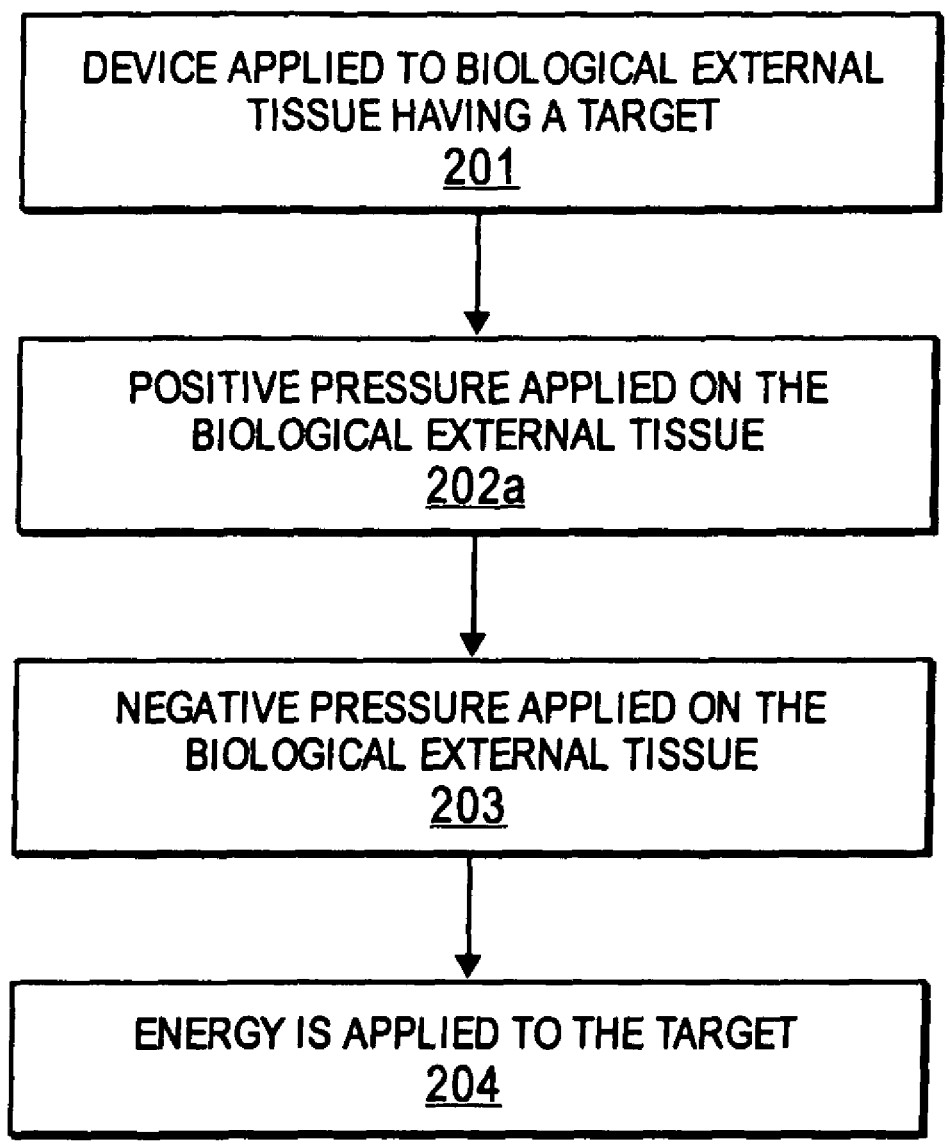
FIG. 2a is a process flow diagram showing a method of applying positive pressure and negative pressure to biological external tissue having a target, according to one embodiment.

Prior to describing specific devices which are embodiments of the invention, several methods which are also embodiments of the invention will be described. FIG. 2a is a process flow diagram showing a method of applying positive pressure and negative pressure to biological external tissue having a target. According to one embodiment of the invention, when the negative pressure is applied to the skin and the volume of biological external tissue is pulled into the device, blood is pulled into the dermal plexus and the dermis. In operation 201 a device is applied to biological external tissue having a target. The device may be, for example, the device 400 shown in FIG. 4. According to one embodiment of the invention, the biological external tissue is dermalogical tissue and the device is applied by pressing the device against such tissue to create a sealed region between the device and such tissue. The target is skin lesions in one embodiment of the invention. In another embodiment of the invention, the target is melanin, blood, tattoo ink, and/or collagen. However, the invention is not so limited. The target can alternatively be any biological external tissue requiring treatment by an energy source. In operation 202a of FIG. 2a, a positive pressure is applied to the biological external tissue.

According to one embodiment of the invention, the positive pressure is applied using an object which protrudes from a surface of a body of the device (such as object 401) which surface faces the area to be treated. According to another embodiment of the invention, the positive pressure is a gas such as a cooling gas, which is applied to the biological external tissue. In operation 203 of FIG. 2a, a negative pressure is applied to the biological external tissue. According to one embodiment of the invention, the negative pressure is a vacuum (e.g., a pressure which is less than or substantially less than atmospheric pressure, such as 400 torr). In operation 204 of FIG. 2a, energy is applied to the target inside the biological external tissue. The energy is incoherent light, coherent light, radio frequency, and/or ultrasound, according to various embodiments of the invention. However, the invention is not so limited. The energy source may be a combination of multiple energies such as a radio frequency and a coherent light in some embodiments of the invention. In another embodiment of this invention, pressurized gas is used to force the blood out of the dermal plexus. The positive pressure applied in operation 202a tends to push blood out of the treatment area, thereby reducing the amount of energy absorption by the blood in the treatment area. This pushing of blood normally occurs just before the application of energy to the treatment area.

Figure 2B:
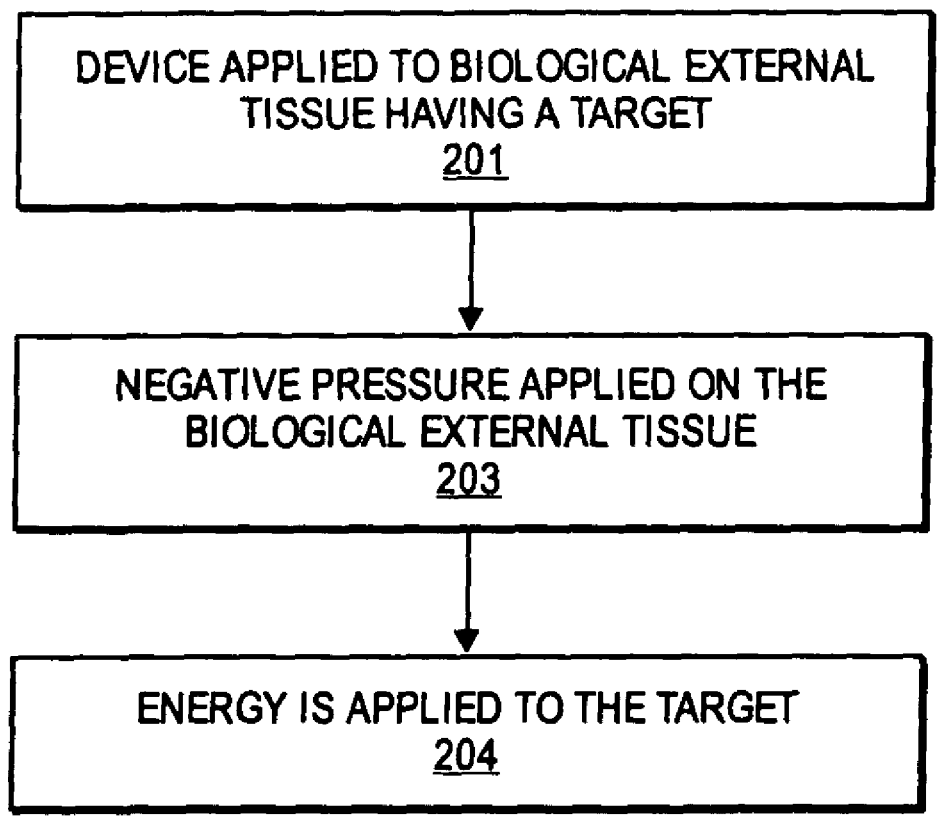
FIG. 2b is a process flow diagram showing a method for applying negative pressure to biological external tissue having a target, according to one embodiment.

FIG. 2b is a process flow diagram showing a method for applying negative pressure to biological external tissue having a target. In operation 201 of FIG. 2b, a device (such as, for example, the device 300 shown in FIG. 3) is applied to biological external tissue having a target; operation 201 of FIG. 2b may be similar to operation 201 of FIG. 2a. In operation 203 of FIG. 2b, a negative pressure is applied to the biological external tissue. In operation 204 of FIG. 2b, energy is applied to the target, which may be energy as described with reference to FIG. 2a. In FIG. 2b, no positive pressure is applied to the biological external tissue prior to the negative pressure being applied.

Figure 2C:
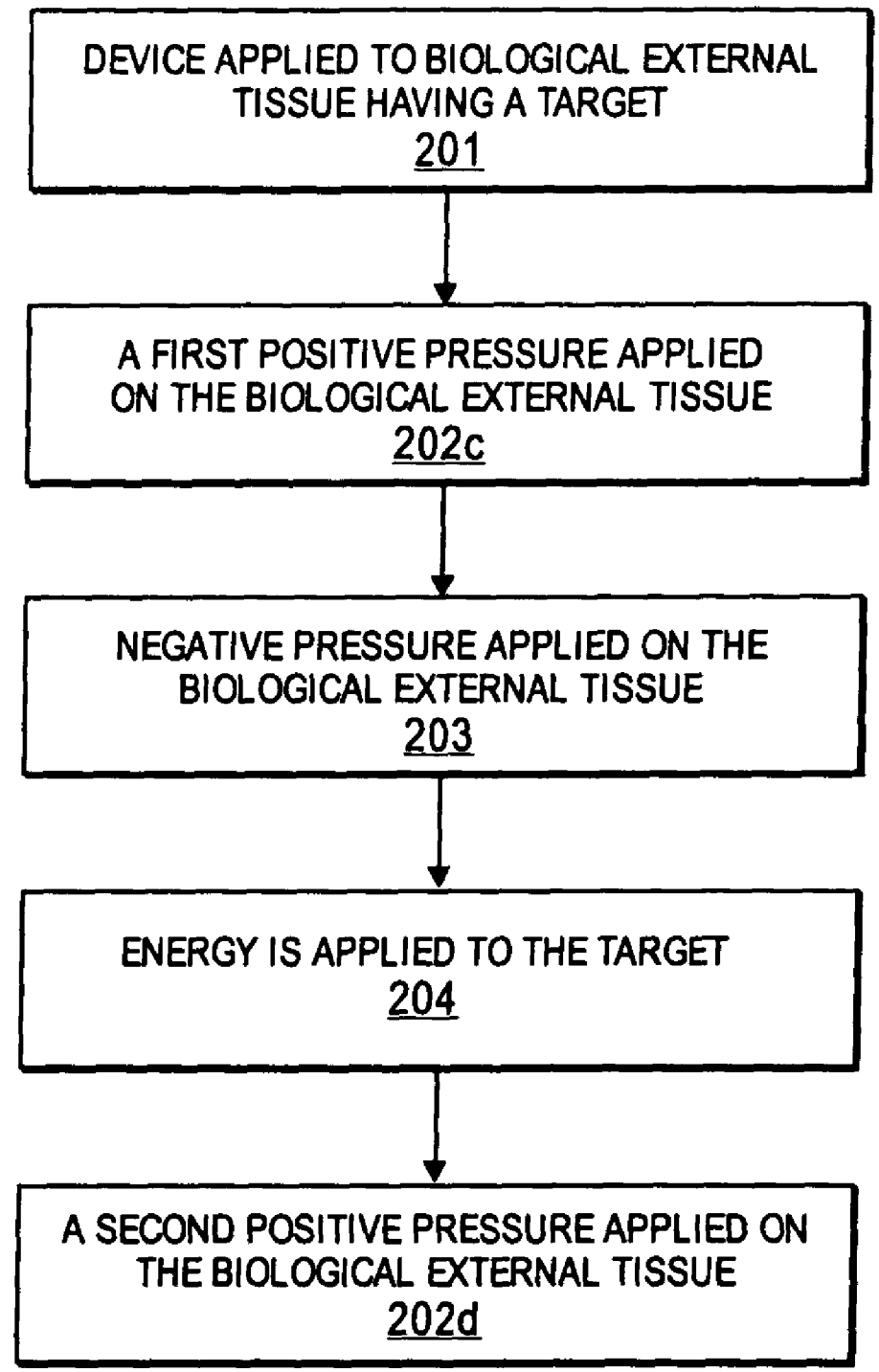
FIG. 2c is a process flow diagram showing a method for applying a sequence of positive pressure, negative pressure, and positive pressure to biological external tissue having a target, according to one embodiment.

FIG. 2c is a process flow diagram showing a method for applying a sequence of positive pressure, negative pressure, and positive pressure to biological external tissue having a target. In operation 201 of FIG. 2c, a device (such as, for example, the device 400 shown in FIG. 4) is applied to biological external tissue having a target, as described with reference to FIG. 2a. In operation 202c, a first positive pressure is applied to the biological external tissue. As described with reference to the method of FIG. 2a, the positive pressure may be a cooling gas and/or an object. In operation 203 of FIG. 2c, a negative pressure is applied to the biological external tissue; this is similar to operation 203 of FIG. 2a. In operation 204 of FIG. 2c, energy is applied to the target; this is similar to operation 204 of FIG. 2a. In operation 202d, a second positive pressure is applied on the biological external tissue. This second positive pressure may be a gas which pushes the device off the biological external tissue, thereby making it easier to release and move the device from the treatment area to the next treatment area. According to some embodiments of the invention, the first positive pressure and the second positive pressure originate from the same pressure source. In some embodiments of the method of FIG. 2c, operation 202c may overlap in time with operation 203 or the sequence may be reversed. Normally, the negative pressure is applied while the energy is applied so operations 203 and 204 overlap substantially in time.

In alternate embodiments of the invention, the first positive pressure and the second positive pressure are different positively applied pressures on the biological external tissue. For example, the first positive pressure is applied by a mechanical object (e.g., object 401) while the second positive pressure is applied by pumping a gas (e.g., air) into the recess between the device and the skin and/or other biological external tissue. In some embodiments of the process flows of the invention, as shown in FIGS. 2a, 2b and 2c, the number of uses of the device is kept track of to determine usage patterns of the device. The energy used in the methods of FIGS. 2a, 2b, and 2c, may originate from a source that is not exposed to any negative and/or positive pressure according to at least one embodiment of the invention. In another embodiment of the invention, generating a peripheral vacuum seal to keep the device on the area of biological external tissue can also be performed and is described further below.

The energy may be an electrical current that is applied to the area of biological external tissue before the blood concentration in the area returns to a normal state (or higher than normal state), according to some embodiments of the invention. Furthermore, measuring color of the biological external tissue can alternatively be performed in some embodiments of the methods shown in FIGS. 2a, 2b and 2c. Similarly, measuring temperature of the biological external tissue may also be performed in some embodiments of the methods shown in FIGS. 2a, 2b and 2c. The device may display at least one measurement of a sensor on the device in some embodiments of the invention. According to one embodiment of the invention, temperature can be measured by monitoring the change in electrical impedance of the treatment volume. The device may be a handheld device in some embodiments of the invention. In other embodiments, a power source may provide power to the device and generate the positive pressure and/or negative pressure through a pressure source connected to the device through a cable element.

In some embodiments of the invention, the power level (e.g., strength) of the energy may be automatically regulated by a controller. The controller may also perform other functions. The controller may, for example, contain a timer that is monitoring the elapsed time since a positive pressure is applied to the treatment volume, according to one embodiment of the invention. The result of a large elapsed time is a pool of blood that returns to the surface of biological external tissue such as skin. All skin types including type VI assume a more reddish appearance. The presence of this pool of blood significantly impacts the therapy. The blood absorbs much of the light energy particularly if the energy is in the visible portion of the spectrum. If the target such as a hair follicle, a tattoo, and/or collagen is deeper in the body than the pool of blood, the therapy is unsuccessful as the majority of the treatment energy is absorbed in the pool of blood before reaching the intended target.

Based upon clinical measurements, the blood volume in the dermal plexus and dermis is reduced for a period time before it refills the capillaries and other vessels in these regions. This period of time is on the order of 100 msec, but varies from individual to individual. By monitoring the elapsed time since application of a positive pressure, the treatment (e.g., application of energy) can be performed in this time period before the blood refills this tissue.

After the controller determines the tissue is in place and, if required, the elapsed time is less than the blood refill time, the therapy is applied to the volume of skin contained inside the device. If photo-therapy is used, an intense light such as from a laser and/or a flash lamp is directed onto the treatment area of the biological external tissue. If rf therapy is used, an electrical voltage is applied to the electrodes and current is passed through the volume of tissue between the electrodes. Once the therapy is completed, the negative pressure is removed and the skin returns to its normal state.

A controller may function in the following manner in the case of a device 400 of FIG. 4. This particular device 400 may provide a positive pressure whenever it is being moved from one treatment area to another treatment area. As noted above, the device typically has a recessed area which faces the skin and which is enclosed by the device and the skin when the device is pressed against the skin. The positive pressure (e.g., from a gas) is typically emitted from the recessed area, and this positive pressure will cause a pressure buildup when the device is pressed against the skin to create a seal between the device and the skin. When the device is being moved, there is no seal and thus no pressure buildup between the skin and the device. When it is pressed against the skin, the positive pressure (e.g., a pressure greater than atmospheric pressure) between the device and the skin will be measured by a pressure sensor, and this indicates to the controller that the movement of the device has stopped and that the user has positioned the device over a desired treatment area. At this point, the controller may be programmed as built to automatically shut off the positive pressure and begin drawing a vacuum against the skin to lock the device in place over the desired treatment area. Alternatively, the controller may be programmed and/or built to merely stop the positive pressure (e.g., shut off the flow of a gas into the recess which creates the positive pressure) but not start a vacuum until the user of the device switches a vacuum on. This alternative implementation gives the user a chance to adjust the positioning before turning the vacuum on by a command from the user.

The biological external tissue that is outside of the device may be prevented from stretching in some embodiments of the methods shown in FIGS. 2a, 2b and 2c. A technique for preventing this stretching is described below.

Figure 3:
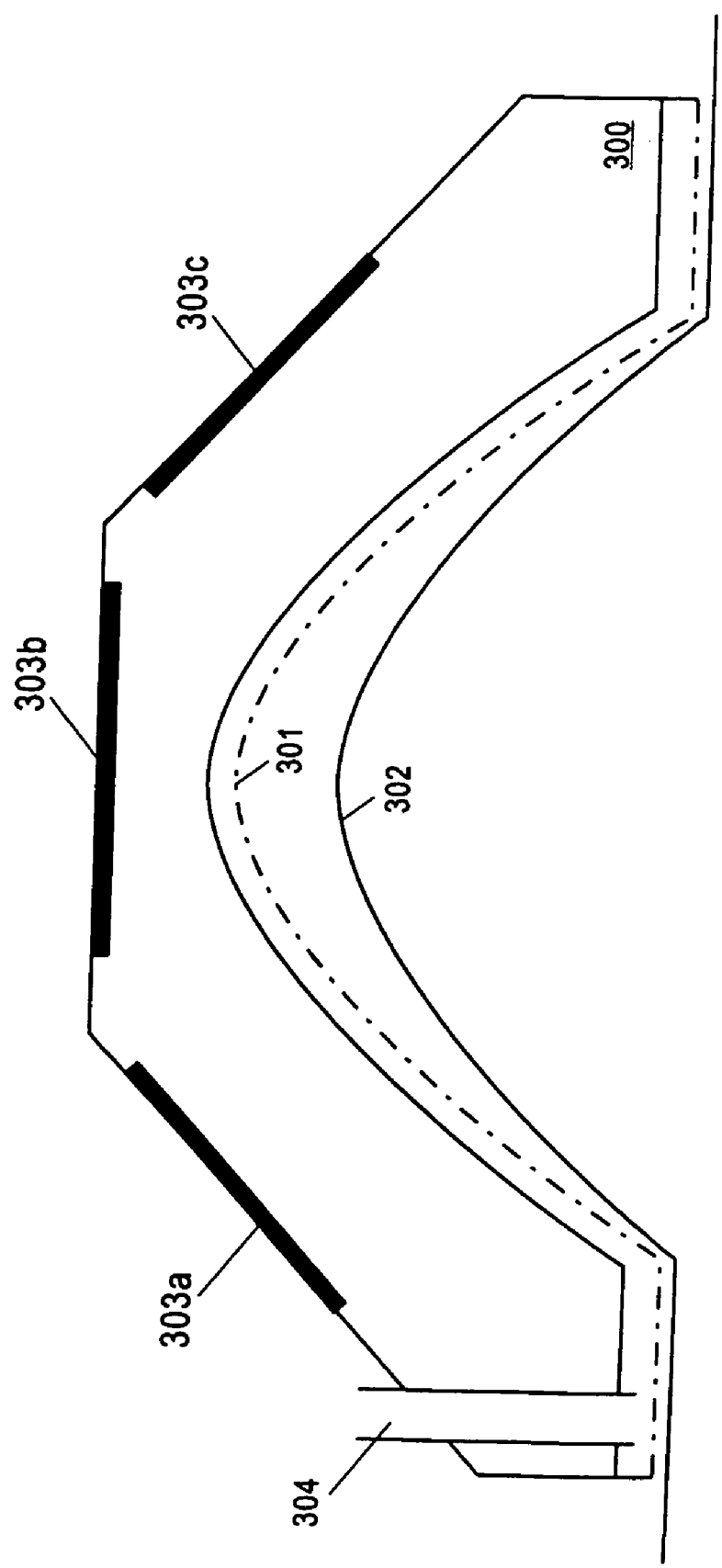
FIG. 3 is a cross-sectional view of a device 300 having multiple light sources 303a, 303b, and 303c, and a pressure conduit 304, according to one embodiment.

FIG. 3 shows, in cross-sectional view, a device 300 having multiple light sources 303a, 303b, and 303c, and a pressure conduit 304. The light sources are contained within a housing and/or body which also includes a cover (which is transparent in the case of light sources) and which separates the light sources from any vacuum generated between the skin and the device). The cover is disposed between the membrane 301 and the light sources 303a-303c. A handle which is coupled to the body may also be included so that a user of the device can easily hold and move the device over a patient's skin and/or other biological external tissue.

A recess and/or void exists between the membrane 301, which faces the biological external tissue 302, and the biological external tissue 302 shown in FIG. 3. Pressure conduit 304 generates a negative vacuum through membrane 301 to bring the biological external tissue 302 into the recess and toward the membrane 301. Membrane 301 can be used to collect dead skin, according to one embodiment of the invention. The membrane 301 is coupled to the conduit 304 to receive the suction from a vacuum pump (not shown) which is coupled to the conduit 304. Light sources 303a, 303b and 303c in FIG. 3 are connected to an energy source that is not shown on the figure, according to one embodiment of the invention. This energy source is not exposed to any pressure through the pressure conduit 304, according to one embodiment of the invention. These light sources are shielded from any negative (or positive) pressure by the cover which is optically transparent in the case where the energy sources provide visible light. It will be appreciated that the light sources may alternatively be other types of energy sources (e.g., microwave radio frequency energy) which may not require an optically transparent cover.

The energy applied to biological external tissue 302 through device 300 is transferred through light sources 303a, 303b and 303c. The light sources 303a, 303b, and 303c may include, for example, light emitting diode (LED) lasers of different wavelengths, thus providing different energy sources, due to the different wavelengths, in the body of the device. Each light source (e.g., source 303a and/or 303b and/or 303c) may be a panel of multiple LED lasers which may be the same type of LED (to produce the same wavelength) and/or may be a panel of multiple LED lasers which may be a different type of LED (to produce different wavelengths). The three panels shown in FIG. 3 (light sources 303a, 303b, and 303c) are arranged within the body of device 300 to provide a spatially uniform lighting at the target so that the intensity of light, at any point over an area which includes the target, is substantially the same. It can be seen from FIG. 3 that the panels (e.g., light source 303a) transmit light directly to the target without any intervening optical fibers and/or waveguides.

This energy for device 300 can be incoherent light, coherent light, and/or alternatively non-visible light and/or electromagnetic radiation in the range of a radio frequency spectrum, and/or ultrasound, according to various embodiments of the invention. The energy source for the device 300 may be a flash lamp, arc lamp, high frequency electrical energy, rf energy, an LED and/or a Direct Current electrical energy, according to various embodiments of the invention. However, the invention is not so limited. The present invention can be multiple combinations of different energies which are provided by energy sources in the body of the device 300. The device 300 may also be connected to a pressure source in the device 300 for providing power to the device 300 and generating pressure through a pressure conduit 304 in one embodiment of the invention. In another embodiment of the invention, the device 300 may be a handheld device that is connected to the pressure source (through a cable element), where the pressure source and power source is separate from the handheld device. In addition, a controller on and/or near device 300 may control the strength of the energy applied through the light source 303a, 303b and/or 303c. According to one embodiment of the invention, there are three light sources, however, any number of light sources is contemplated by the present invention. In one embodiment of the invention, a tapered outer wall on the periphery of device 300 prevents the biological external tissue 302 that is outside the device 300 from stretching.

Stretching the skin (1) reduces the concentration of melanin in the epidermis, (2) reduces scattering in both the epidermis and the dermis, and (3) moves the treatment target closer to the surface. Vacuum provides an excellent mechanism for stretching the skin. By sealing on an area of skin, and generating a vacuum, the skin is drawn and stretched much more than can be done manually.

Figure 4:
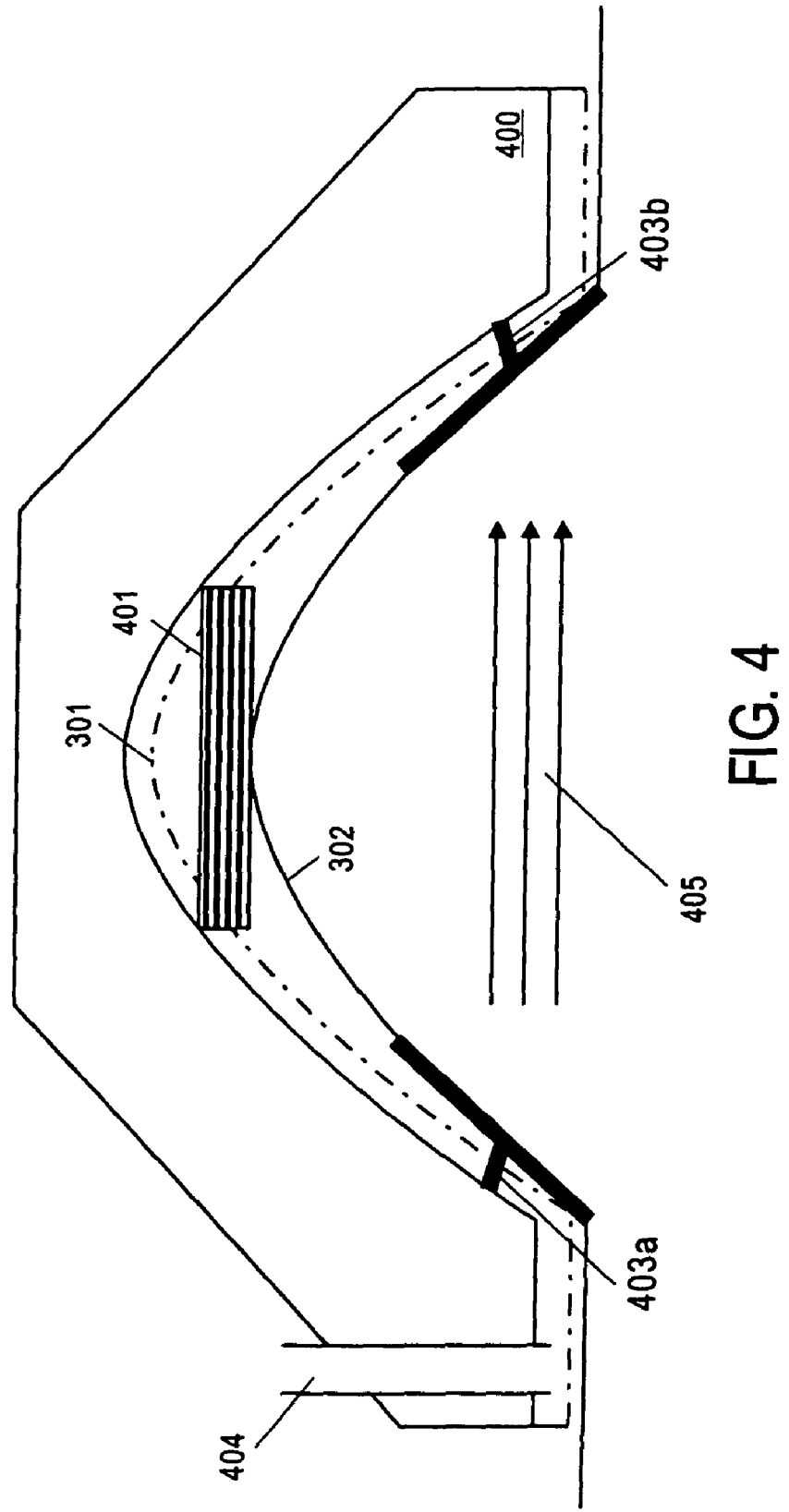
FIG. 4 is a cross-sectional view of a device 400 having a pair of electrodes 403a and 403b, an object 401, a pressure conduit 404 and an electric current passing through biological external tissue 302, according to one embodiment.

FIG. 4 shows, in cross-sectional view, shows a device 400 having a body which is coupled to a pair of electrodes 403a and 403b, and the body supports an object 401 which protrudes into a recess of the body. A pressure conduit 404, which is coupled to the body, generates a positive and/or negative pressure on biological external tissue 302. The object 401 is designed to be brought into contact with biological external tissue 302 either before and/or while a negative pressure through pressure conduit 404 is applied, thereby drawing the skin into the recess and into contact with the object. The object is used for pressing onto the biological external tissue 302 and forcing the blood out of the dermal plexus, according to one embodiment of the invention. The object 401 may be stationary relative to the body and/or it may move, like a plunger and/or piston, down from the body and toward the skin. A stationary object is simpler and easier to build but will require that the vacuum draw the skin sufficiently into contact with the object. The moving object can provide more force and the recess can be larger. The object 401 may be transparent in the optically visible spectrum, thereby allowing light to pass through it in those embodiments (such as, e.g., the device of FIG. 5) which include light sources which emit light that must pass through the object to reach the target.

According to some embodiments of the invention, pressure conduit 404 generates a positive pressure that is a gas, which may be a cooling gas. According to one embodiment of the invention, the gas that is used to apply pressure to the biological external tissue 302 to force the blood out of the dermal plexus and the dermis may also be used to assist in releasing the device 400 from the biological external tissue 302. In another embodiment of the invention, the cooling gas is applied before applying an electric current 405 through the biological external tissue 302 through electrodes 403a and 403b. In another embodiment of the invention, the pressure conduit 404 generates a peripheral vacuum seal to hold the device 400 on biological external tissue prior to generating a vacuum in the recess of the body.

The object 401 that applies pressure to the biological external tissue 302 to force the blood out of the dermal plexus and the dermis may be cooled to a temperature lower than the epidermis, according to one embodiment of the invention. Without cooling, the normal epidermis starts at a temperature between 31 degrees Celsius and 33 degrees Celsius, according to one embodiment of the invention. During treatment, it will rise in temperature and may reach a temperature at which burning occurs. If the epidermis starts at a temperature lower than normal, it can change in temperature during treatment more than uncooled skin before it reaches a temperature at which burning occurs.

The gas that is used to apply pressure to the biological external tissue 302 to force the blood out of the dermal plexus and the dermis may be cooled to a temperature lower than the epidermis, according to one embodiment of the invention. The benefit of this cooling with pressurized gas is the same as the benefit obtained with a cool object 401. The object 401 that applies pressure to the biological external tissue 302 to force the blood out of the dermal plexus and the dermis may contain an optical coating to control the wavelengths of light that are used in the treatment, according to another embodiment of the invention. In some embodiments of the invention, the object 401 that applies pressure to the skin to force the blood out of the dermal plexus and the dermis may contain an optical coating to control the energy of the light that is used in the treatment. According to one embodiment of the invention, DC or AC or capacitance electrical sensors 403a and 403b are used to determine if the biological external tissue 302 is properly positioned in the device 400.

The device as shown in FIG. 4 can include various sensors such as skin color sensors, temperature sensors, and capacitance sensors on the device in some embodiments of the invention. Furthermore, the device shown in FIG. 4 may have a tapered outer wall on the periphery of the device that prevents the biological external tissue 302 that is outside of the device 400 from stretching, similarly to as described with reference to FIG. 3. Other features from other embodiments described herein may also be added to the device as shown in FIG. 4.

The electrodes 403a and 403b in FIG. 4 can serve two purposes. One purpose is for applying rf treatment energy according to one embodiment of the invention. The second purpose is as an electrical sensor, according to a different embodiment of the invention. An AC or DC voltage is applied to at least two of the electrical sensors in other embodiments of the invention. When the biological external tissue 302 contacts two of the electrical sensors 403a and 403b, an electrical current 405 passes between the two electrodes 403a and 403b. When a sensor within device 400 detects the current 405, it signals a controller within and/or outside device 400. The controller interprets this signal to mean that the biological external tissue 302 is properly positioned according to one embodiment of the invention. This can serve as a secondary skin detection system for added safety, according to at least one embodiment of the invention.

Figure 5:
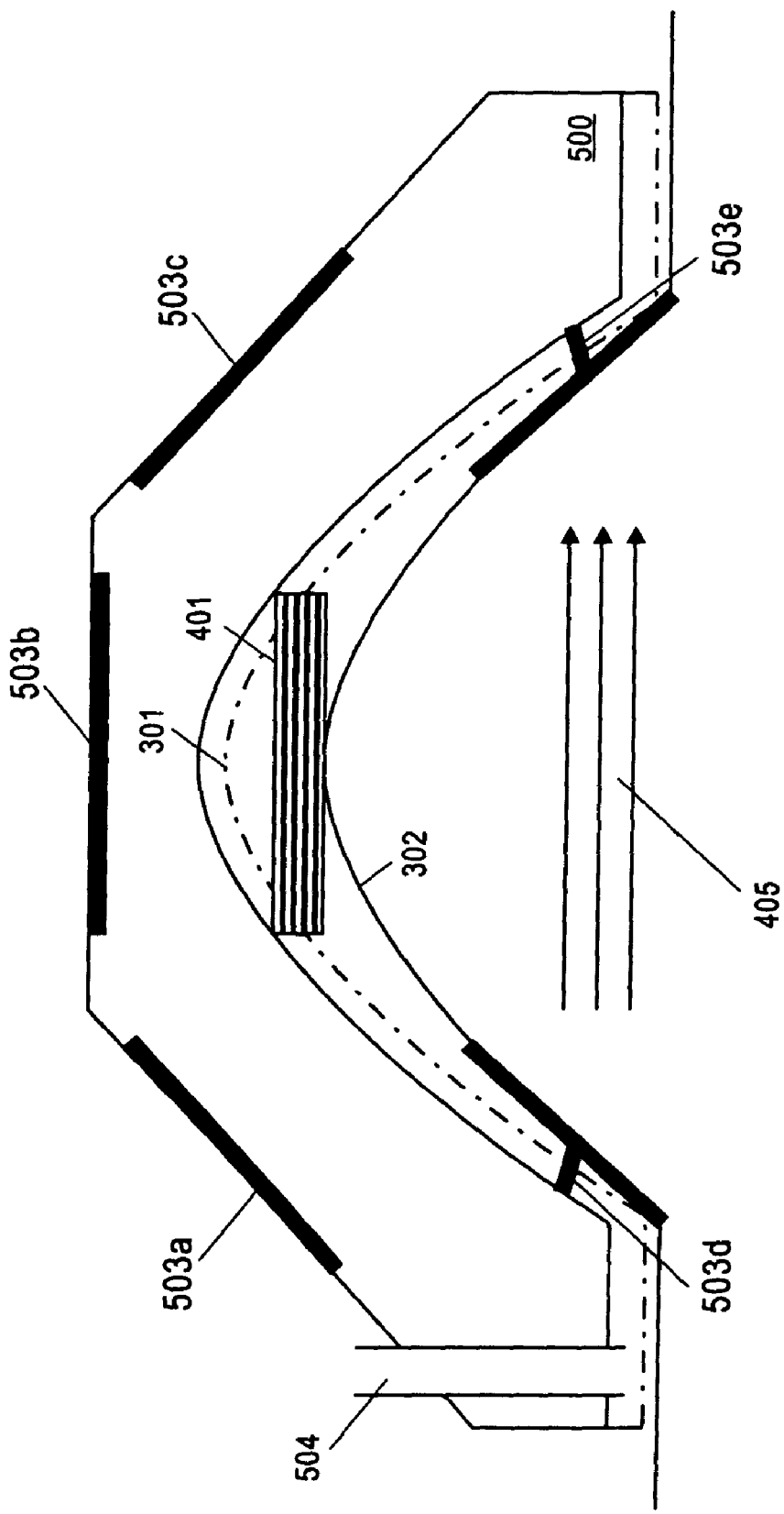
FIG. 5 is a cross-sectional view of a device 500 having multiple energy sources 503a-c, an object 401 and a pressure conduit 504, according to one embodiment.

FIG. 5 shows in cross-sectional view, a device 500 having multiple energy sources 503a-c, an object 401 and a pressure conduit 504. In a typical treatment, the device 500 is pressed against the skin, and the skin is drawn into the recess of the body of device 500 as shown in FIG. 5. According to one embodiment of the invention, the device 500 generates a positive pressure against the skin (through the object 401) followed by a negative pressure (through a vacuum pump coupled through a valve to conduit 504), and then again a positive pressure (from an air pump coupled, through a valve, to conduit 504) to be applied to biological external tissue 302 through pressure conduit 504. The positive pressure from the object 401 may be done concurrently with the generation of a vacuum (negative pressure) in the recess. This sequence helps certain treatment procedures of biological external tissue 302 requiring blood within the biological external tissue 302 to be pushed away prior to the treatment. FIG. 5 differs from FIG. 3 and FIG. 4 in that the device shown in FIG. 5 can generate both an electric current through electrodes 503d and 503e (to either sense the device's contact with the skin and/or to deliver electrical energy as a treatment) and can apply energy through sources 503a, 503b and 503c on device 500. The energy sources 503a, 503b, and 503c may be similar to the sources 303a, 303b, and 303c. However, the energy through energy sensors 503a, 503b and 503c is not limited to light, according to one embodiment of the invention as shown in FIG. 5. The pressure conduit 504 generates at one point in time in a treatment sequence, a positive pressure comprising a gas in an area of the biological external tissue 302 in FIG. 5. However, the pressure conduit 504 can alternatively generate negative pressure at a different time in the sequence by switching a valve which connects the conduit to either an air pump and/or a vacuum pump. Other features (such as, e.g., skin color sensors, a display, etc.) from other embodiments described herein may also be implemented on the device as shown in FIG. 5.

In FIG. 5, a high frequency rf electrical current 405 enters the body from one electrode 503d, passes through a layer of biological external tissue 302 and exits the body at a different electrode 503e. FIG. 5 shows a potential pathway through the biological external tissue 302 for this current 405. As the current 405 passes through the body, it tracks a path through the least resistive tissues. Blood is the most conductive biological entity and hence the rf electricity tends to track the blood vessels. This is fine if the target for the rf is the blood, but if the target is the adjacent tissue such as collagen, the presence of the blood can defeat the intended therapy.

Figure 6:
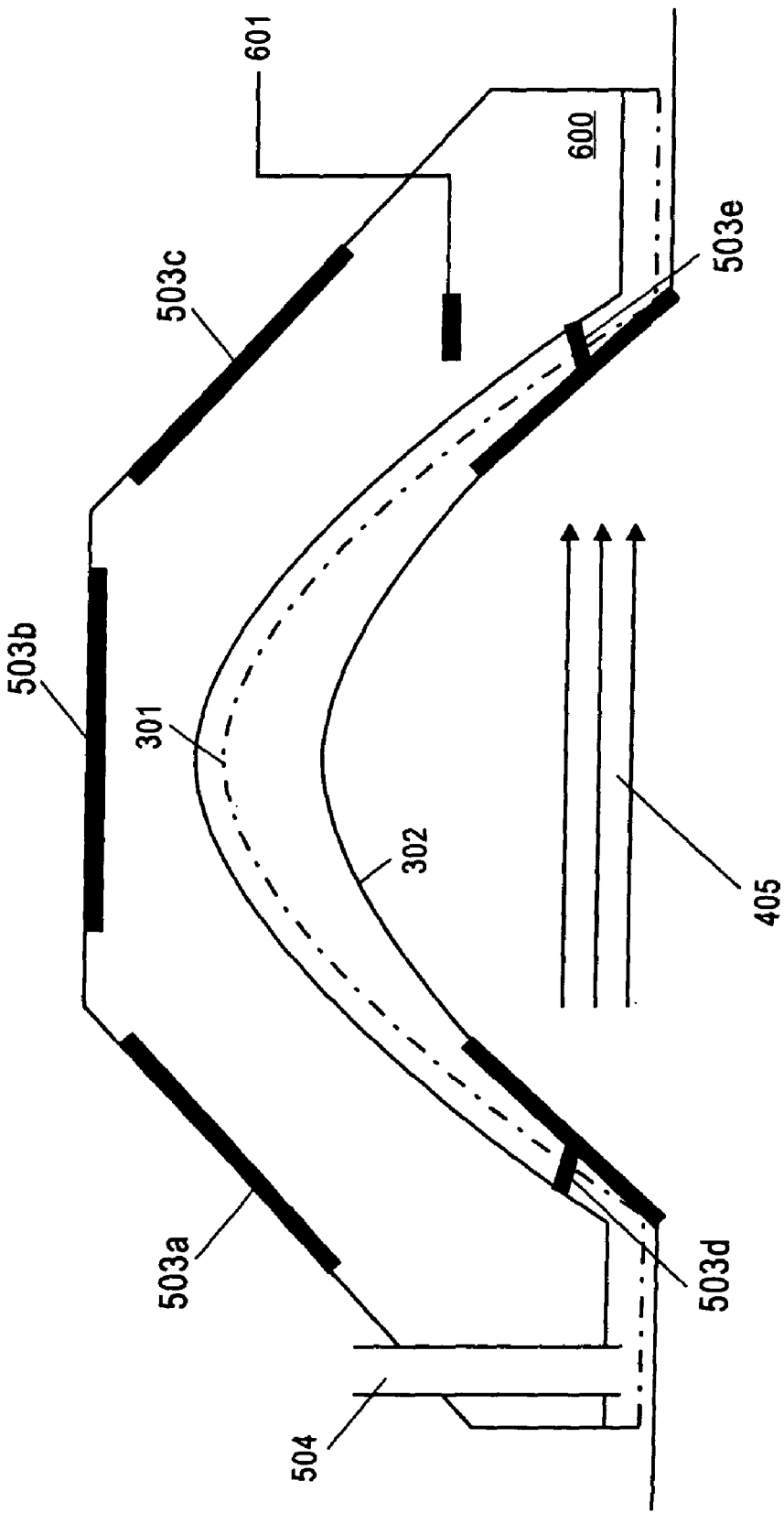
FIG. 6 is a cross-sectional view of a device 600 having multiple energy sources 503a-c, a pressure conduit 504, and a skin temperature sensor 601, according to one embodiment.

FIG. 6 shows in cross-sectional view, a device 600 having multiple energy sources 503a-c, a pressure conduit 504, and a skin temperature sensor 601. The skin temperature sensor 601, as shown in FIG. 6, is a capacitance sensor. It may be placed on the membrane 301 rather than within the body of the device. In one alternative embodiment of the device 600, an object 401 may also be used, as shown with reference to FIG. 4. Furthermore, other features from other embodiments described herein may be added to the device 600 shown in FIG. 6. The skin temperature sensor 601, as shown on device 600 in FIG. 6, is used to measure the temperature of the biological external tissue 302 to prevent burning when applying energy through one or more of energy sources 503a-c to biological external tissue 302.

According to one embodiment, the skin temperature sensor 601 is a non-contact skin temperature sensor that monitors the infrared light emitted from the surface of the biological external tissue 302 and translates this into a surface temperature. The information from the skin temperature sensor 601 is sent to a controller which is within the body of the device 600 in certain embodiments of the invention. The controller is a micro controller and/or microprocessor that interprets the skin temperature, and if the temperature has reached a dangerous level, the micro controller terminates the application of energy in one embodiment of the invention According to another embodiment of the invention, the controller is a software controlled micro controller and/or microprocessor.

Figure 7:
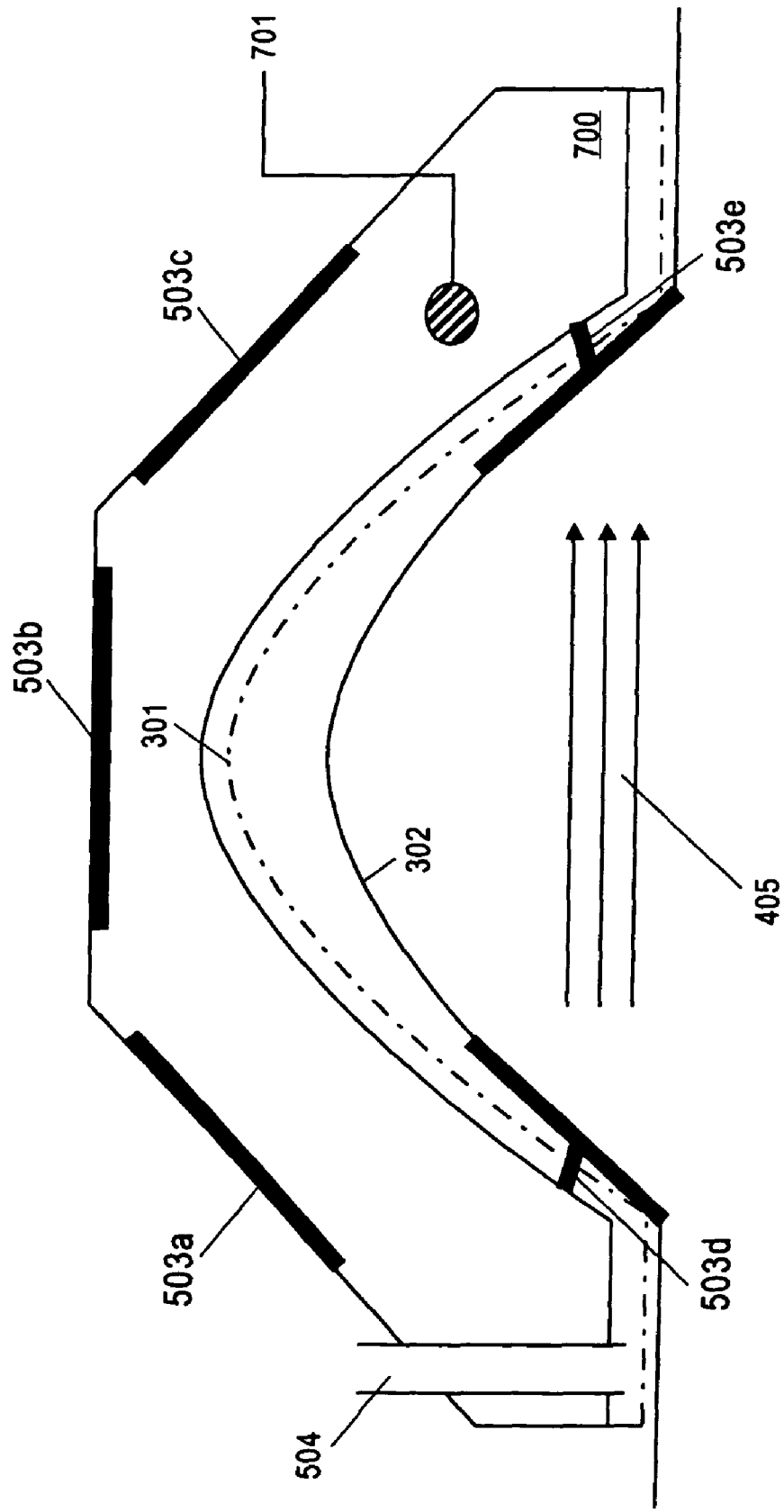
FIG. 7 is a cross-sectional view of a device 700 having multiple energy sources 503a-c, a pressure conduit 504, a membrane 301, electrodes 503d and 503e, and a skin color sensor 701, according to one embodiment.

FIG. 7 shows in cross-sectional view, a device 700 having multiple energy sources 503a-c, a pressure conduit 504, a membrane 301, electrodes 503d and 503e, and a skin color sensor 701. FIG. 7 differs from FIG. 6 in that it does not have a skin temperature sensor 601, but rather has a skin color sensor 701. The skin color sensor 701 is used to measure the level of energy that needs to be applied to biological external tissue 302 based upon the color of the skin and corresponding melanin and blood levels within biological external tissue 302. Other features (such as, e.g., an object 401, etc.) from other embodiments described herein, may be added to the device shown in FIG. 7.

The skin color sensor 701 consists of a light source and a photodiode. By shining the light source on the surface of the biological external tissue 302 and reading its reflection with the photodiode, the skin color can be determined. The light source may be adjacent to the photodiode (as shown), or it may be separated from it. Determining the skin color prior to treatment is important. Even with stretching, dark skin is still more susceptible to burning than lighter skin. Consequently the treatment energy may be adjusted based upon the readings of the skin color sensor. For darker skin, the treatment energy is lowered. For lighter skin, the treatment energy is raised.

Clinical tests of device 700 on lighter skin types shows that the skin color sensor (4) can also be used to detect the absence of the blood and further detect the refill of the vessels in the dermal plexus and dermis. Prior to stretching the biological external tissue 302, such as skin, into the device 700, the skin color is measured. As the skin is stretched and the blood is removed from the dermal plexus, the reflected light detected by the photo diode increases due to less absorption by the blood. As the dermal plexus refills, the reflected signal decreases due to increase absorption by the blood. The skin color detection device monitors this change and notifies a control system within and/or outside the device 700, according to certain embodiments of the invention.

Stretching the epidermis reduces the concentration of melanin. To understand this phenomenon, consider a colored balloon. The pigmentation in the balloon gives it its color. The melanin pigmentation in our skin gives us our color. When a colored balloon is deflated, it is difficult or impossible to see through it. It is opaque. As the balloon is inflated, it becomes more transparent. The elastic portion of the balloon stretches. The inelastic portion, such as the pigment, does not stretch. Its concentration is reduced and the balloon becomes more transparent. The same happens in our skin. The melanin is less elastic that the interstitial components. These tissues stretch while the melanin does not. As the concentration of melanin drops, the skin becomes whiter. In fact, by stretching the skin of a dark individual, the skin becomes quite pink as the underlying vascular system becomes exposed.

The second advantage of stretching the skin prior to and during treatment with intense light sources is the reduction in scattering. When light enters human tissue, it is immediately scattered in all directions by the collagen, fibrous tissue and other intercellular constituents. Much of this light is scattered back to the surface and out of the body. Much is scattered sideways and thereby reduces the energy density as the cross-section of the intense light source increases. The level of scattering is directly proportional to the concentration and orientation of the intercellular material. Stretching the skin reduces the concentration of these materials in direct proportion to the level of stretching. The corresponding scattering is subsequently reduced as well.

As described above, the two advantages to stretching the skin is reduced absorption by melanin and reduced scattering. The third advantage is that the treatment target moves closer to the surface. Stretching the skin reduces its thickness. One can see this by taking a rubber band and measuring its thickness. Then stretch the rubber band and measure its thickness a second time. The rubber band is thinner. The same effect occurs with the outer layers of the skin. The epidermis becomes thinner. The dermal plexus becomes thinner. Even the dermis becomes thinner. The target however, remains in the dermis and is now closer to the surface and thus more energy can reach it.

Figure 8:
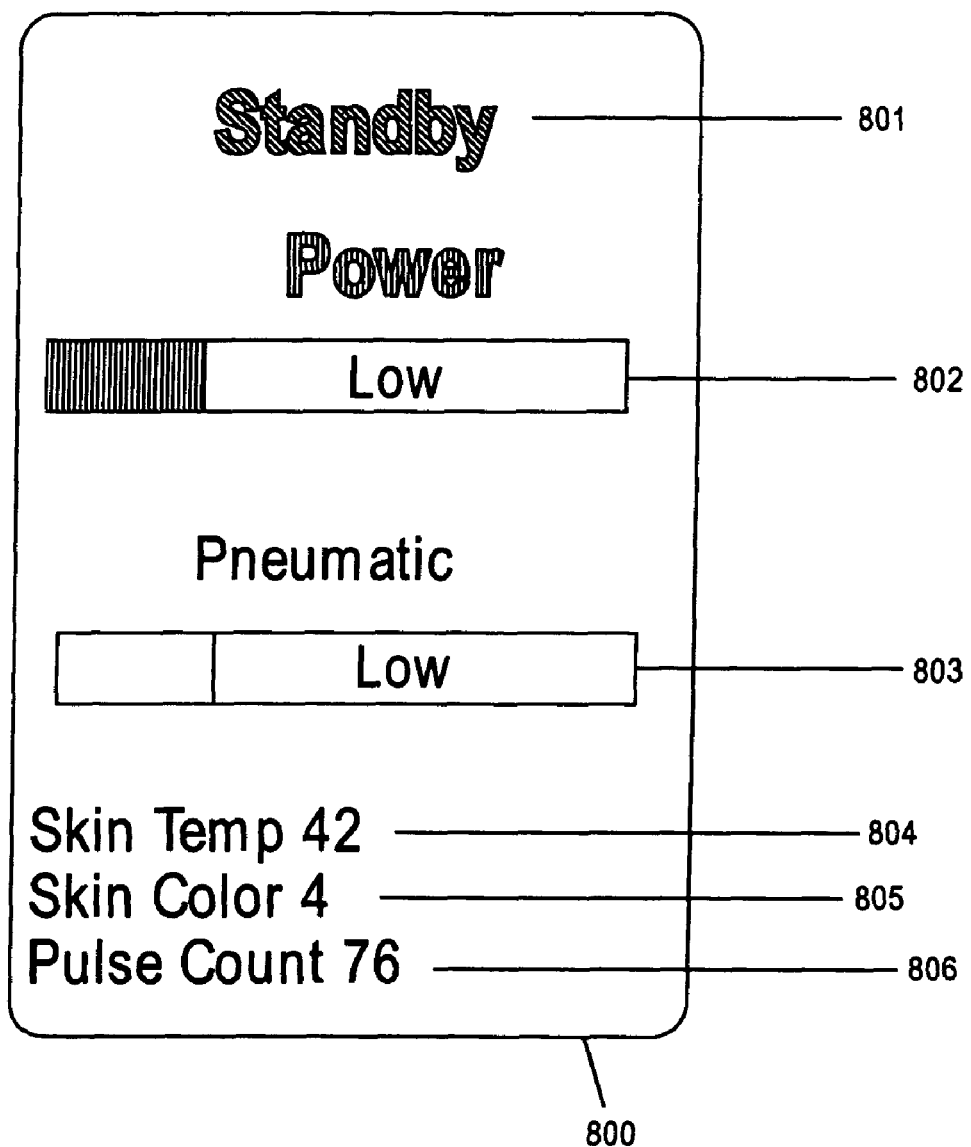
FIG. 8 is an exemplary display 800 on a handheld device according to certain embodiments of the invention.
Figure 9:
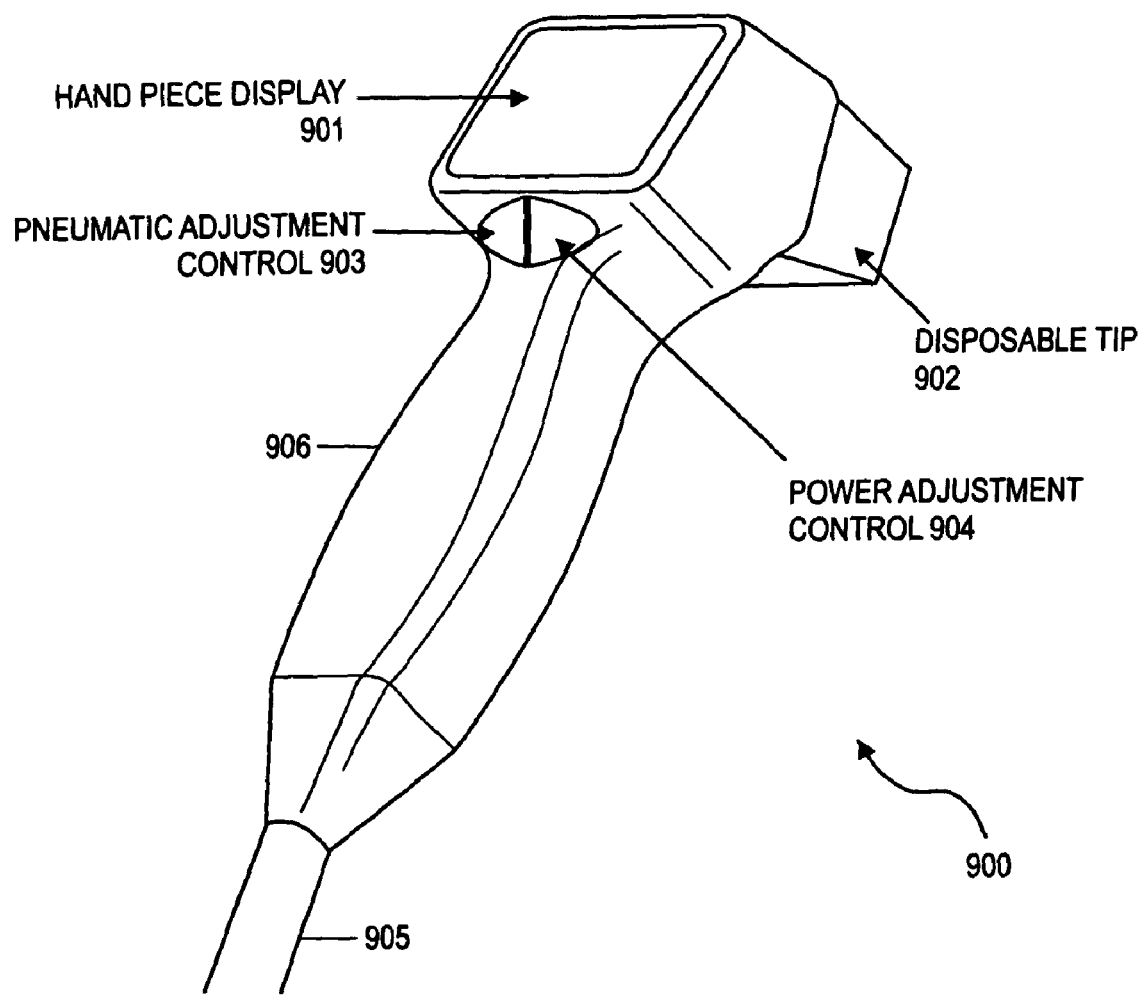
FIG. 9 is a handheld device 900 with a display element 901 that displays at least one parameter with respect to a treatment of the biological external tissue 302, according to one embodiment.

FIG. 8 shows an exemplary display which may be disposed on a surface of a handheld device, such as any of the devices shown in FIGS. 3-7 and 9-11. FIG. 9 shows a perspective view of a handheld device 900 with a display on a surface of the device. The device of FIG. 9 may include the various features described herein, such as multiple energy sources, an object which pushes blood out of the treatment area, one or more pressure conduits, etc. The device 900 includes a pixilated display with multiple rows and columns of pixels on the display 901. An example of the content of such a display is shown in FIG. 8 which shows a display 800 which indicates the status 801 of the device (e.g., "Standby" or "On" or "Treating"), the power status 802 of the device (e.g., Low or Medium or High along with a bar graph which indicates the power status), the vacuum status 803 of the device (e.g., pneumatic level is "Low" or "High"), the skin's temperature 804 (e.g., 42° C.), the skin's color 805 (e.g., 4) and the patient's pulse count 806 (e.g., 76). The display 800, being on the handheld, is easier for an operator (e.g., physician) to see while doing a treatment because the operator can look at the treatment site while operating the device and still be able to see both the site and the display (rather than having to look at a console which has a display and which is separate from the handheld device. The display 901 may be a liquid crystal display (LCD) and/or an LED display which is controlled by a display controller which updates the display's pixels to reflect new information. The device 900 includes a power adjustment control 904 which can be used to control the amount of energy that is applied to the biological external tissue (e.g., to adjusting the intensity of the light from light sources). The device 900 also includes a pneumatic adjustment control 903 to control the strength of a vacuum that is applied through a vacuum pump (not shown) through the device 900 (e.g., (e.g., a pressure which is less than or substantially less than atmospheric pressure, such as 400 torr). Furthermore, the device 900 includes a cable 905 that delivers power and pressures to operate device 900 (e.g., the cable 905 is connected on the other end to a wall power outlet, and/or a standalone central control station); a vacuum through device 900 to be applied to the biological external tissue in front of the disposable tip 902 (e.g., the vacuum may be delivered through conduit 905 along with power by maintaining a separate chamber that separately carries a negative pressure through device 900); a positive pressure to press down on biological external tissue (e.g., carried through a separate chamber than the one that carries the vacuum and power); and the cable 905 may optionally include various electrical wires that deliver signals to and from various sensors (e.g., sensors on the device 900 may include skin temperature sensors, skin color sensors, and capacitance sensors, etc.) on device 900 to a standalone central control station (not shown) in addition to (or rather than) the hand piece display 901. In one embodiment, the standalone central control station may be a computer that has a printer and/or storage device(s) for recording data from the sensors on device 900. The disposable tip 902 on device 900 may be a disposable membrane 301 and/or may be custom designed to fit a particular type of biological external tissue or size of biological external tissue (e.g., the disposable tip 902 may be different for large areas of skin verses small areas of skin, and may be shaped differently to treat areas of biological external tissue that is not purely flat because of contours created by skeletal structures and/or because of hair follicles). The handle 906 of device 900 may be designed to fit a particular size of hand or may have groves to fit a particular hand size in some embodiments. In addition, in other embodiments the handle 906 may be of variable size (e.g., to fit larger and smaller hands, or to reach into areas of biological external tissue that are otherwise difficult to reach). The handle 906 may be removable from the device 900 head (e.g., the head might be the handpiece display 906 and disposable tip 902 together) in one embodiment to allow a user of device 900 to quickly put on different types of sensors, display 901 variations, and disposable tip elements 902.

Figure 10:
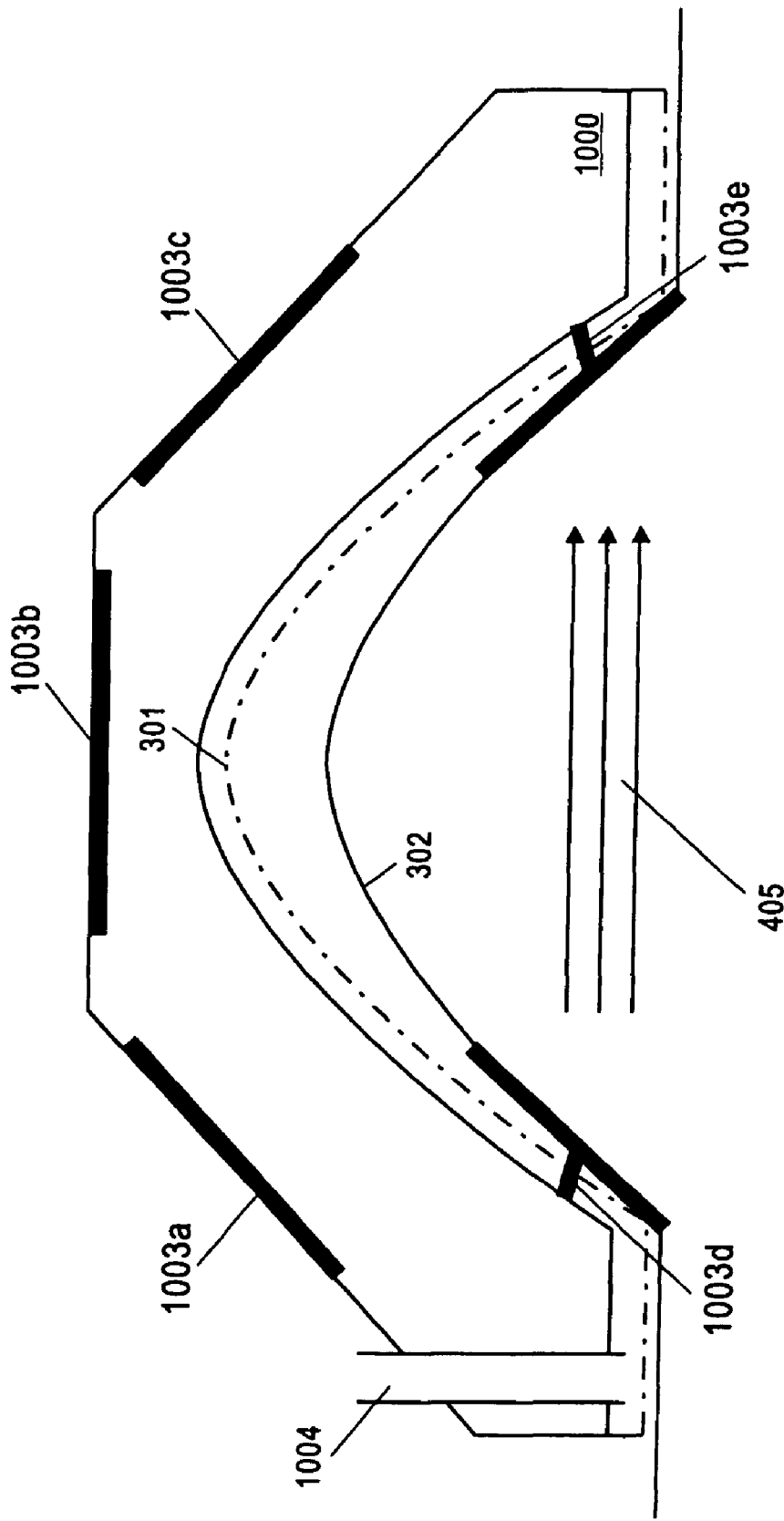
FIG. 10 is a cross-sectional view of a device 1000 having multiple energy sources 503a-503e that are not exposed to any pressure, and a pressure conduit 1004, according to one embodiment.

FIG. 10 shows a device 1000 having multiple energy sources 503a-503e that are not exposed to any pressure, and a pressure conduit 1004. FIG. 10 differs from FIG. 3 in that the device shown in FIG. 10 includes multiple energy sources such as electrodes 1003d and 1003e, while the device shown in FIG. 3 is limited to light based energy only. In one embodiment of the present invention, the pressure conduit 1004 in FIG. 10 generates a negative pressure.

Figure 11:
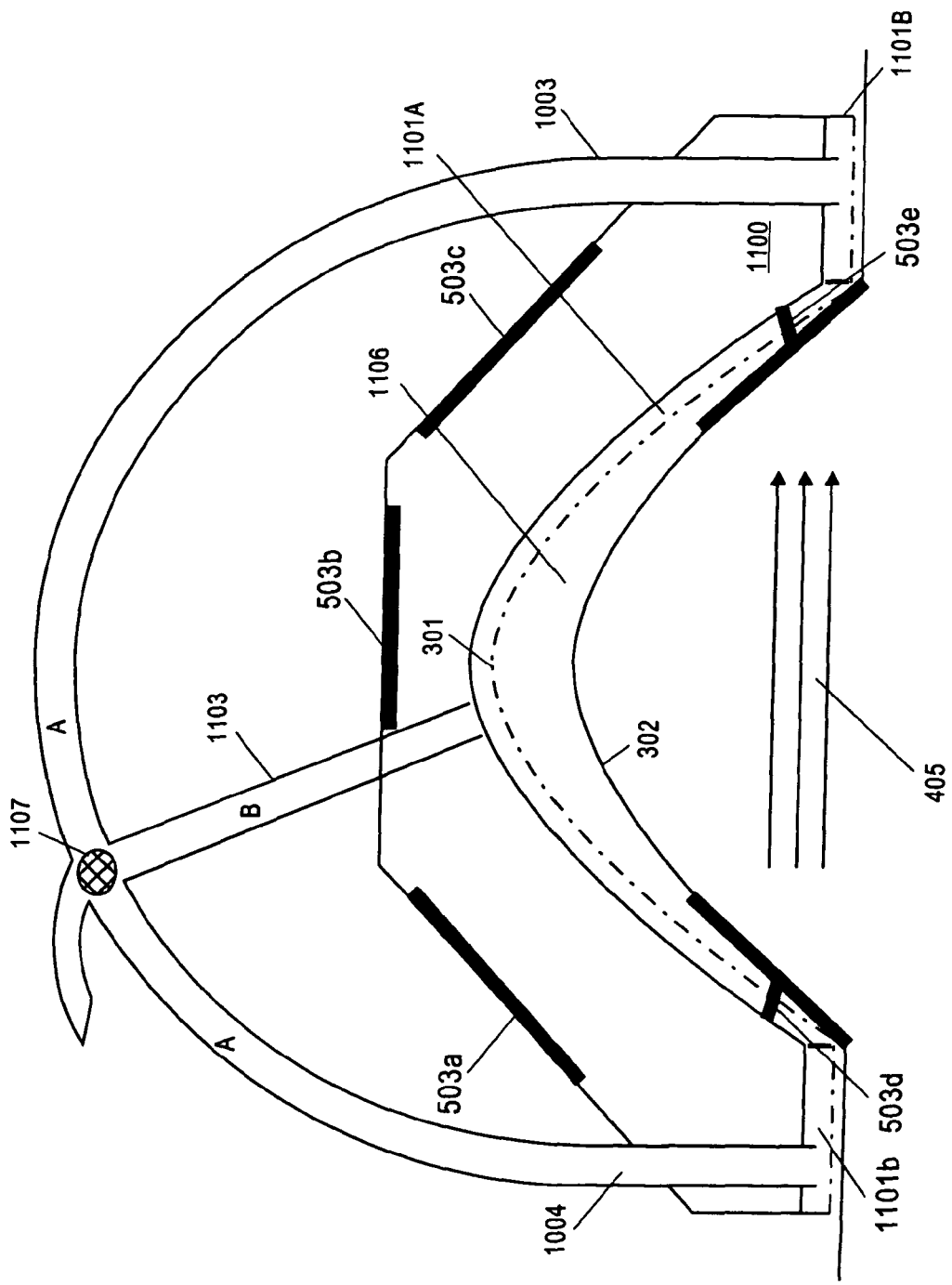
FIG. 11 is a cross-sectional view of a device 1100 having a body that is applied to biological external tissue 302 and multiple vacuum chambers as shown in A and B on FIG. 11, according to one embodiment.

FIG. 11 shows a device 1100 having a body that is applied to biological external tissue 302 and multiple vacuum chambers shown as A and B on FIG. 11. The device 1100 in FIG. 11 applies two vacuum pressures at different times to biological external tissue 302. In other embodiments of the invention as shown in FIG. 11, there are any number of vacuum chambers A, B on device 1100. One pressure A is generated at the periphery of device 1100 through the pressure conduits 1004 and 1003. A second pressure is generated as shown in B through the pressure conduit 1103. The device 1100 includes multiple energy sources 503a, 503b, and 503c and electrodes 503d and 503e. The membrane 301 has two portions: an interior portion 1101A which generates an interior vacuum in the recess 1106 of the body of device 1100 and a peripheral border portion 1101B which generates a peripheral vacuum seal between the flat surface of the periphery of the device 1100 and the skin. A valve 1107 couples the two vacuum chambers together and may be manually controlled by an operator and/or automatically controlled by a micro controller (e.g., micro controller 1303 in the handheld device). Initially, the valve 1107 is set so that a vacuum is generated in only the peripheral border of the device; the peripheral border may be a rectangular frame (resembling a picture frame) or other shapes. This clamps the device to the skin without creating a vacuum in the recess 1106. Then the valve 1107 is switched so that a vacuum is generated in both the peripheral border and the recess 1106 of the device. In an alternative embodiment, the valve may be positioned at the junction between the portion 1101A and 1101B and no separate conduit 1103 is required; in this case the valve is switched open to extend a vacuum from the peripheral border region to the interior region. The advantage provided by a device such as device 1100 is that the skin within the recess can be stretched even more than skin within devices such as device 300 or 400 because less skin outside of device 1100 will be pulled in by the vacuum within the recess. The skin in the peripheral border region is clamped into a relatively fixed position before the skin within the recess is exposed to a vacuum, which tends to prevent skin from being pulled into device 1100 from outside of the device 1100. One or more features (such as, e.g., an object 401, skin color sensors, pressure sensors, a display on the handheld, etc.) from other embodiments described herein may be added to the device 1100 according to certain implementations of the invention.

Figure 12:
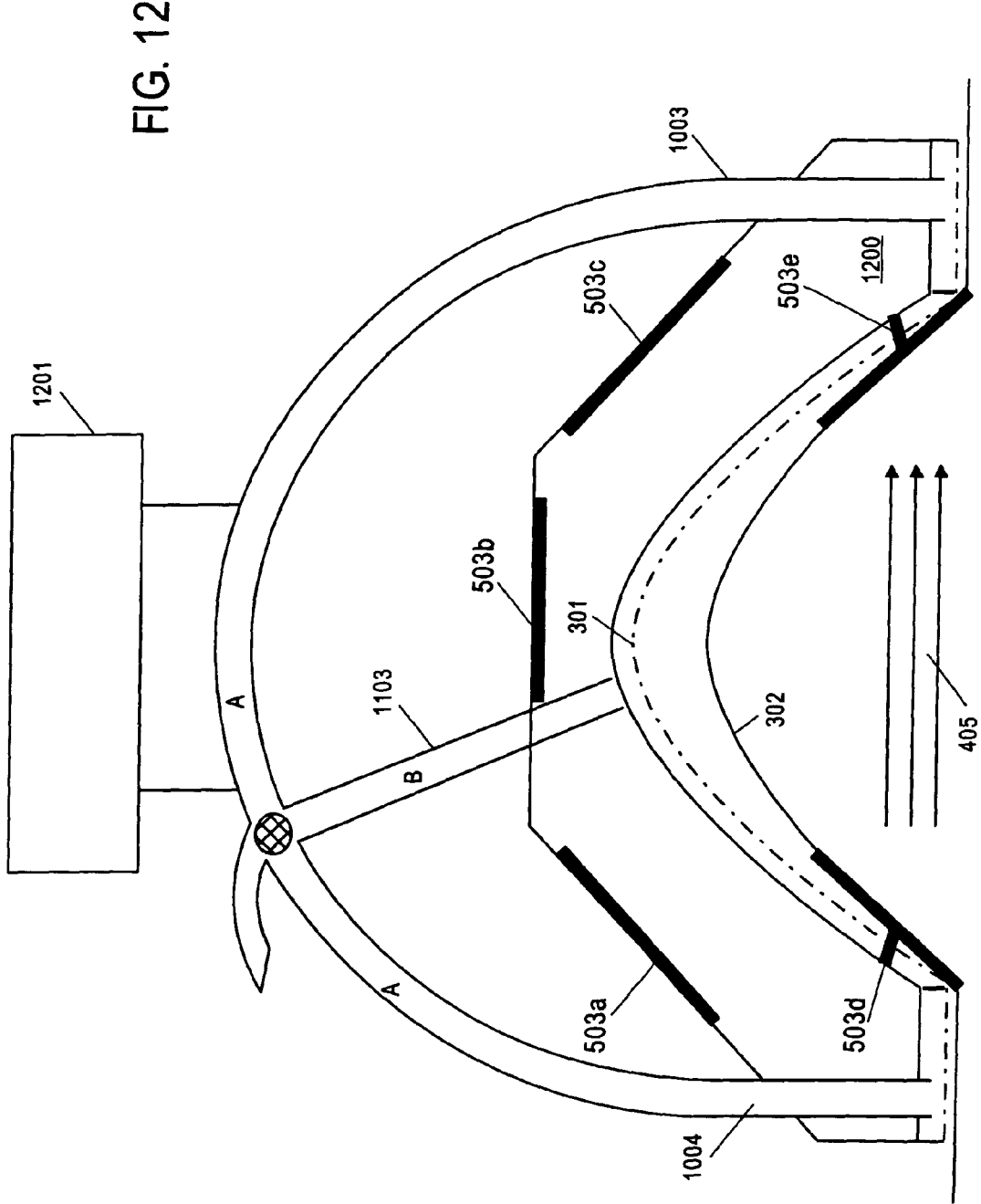
FIG. 12 is a cross-sectional view of an apparatus 1200 that attaches to an existing device 1201 to apply energy to biological external tissue 302 through energy sources 503a-c.

FIG. 12 shows a device that is an apparatus 1200 that attaches to an existing device 1201 to apply energy to biological external tissue 302 through energy sources 503a-c. The apparatus shown in FIG. 12 is an embodiment of the invention that is an add-on to existing device 1201. The apparatus 1200 adds one or more features as described with reference to FIGS. 1-11 in various embodiments of the invention.

Figure 13:
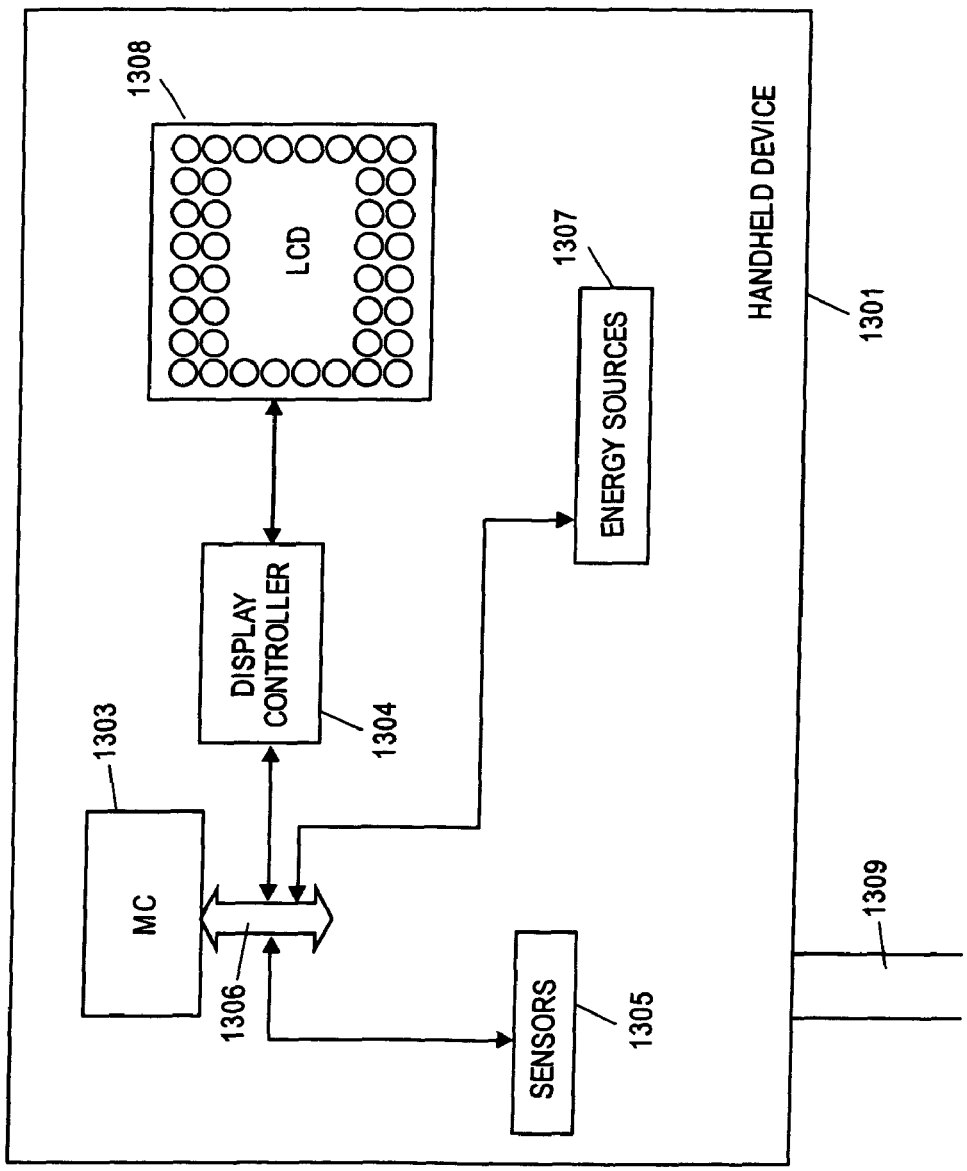
FIG. 13 is an electrical schematic of a handheld device according to one exemplary embodiment.

FIG. 13 shows an electric architecture for a handheld device such as device 900. The device 1301 shown in FIG. 13 includes an LCD display 1308 having multiple rows and columns of pixels. The output of display may be the same as or similar to the output of display 800. The display 1308 is coupled to a programmable or programmed micro controller 1303 through a display controller 1304; it will be appreciated that the display controller 1304 may be eliminated if the micro controller performs the display updating functions of the display controller. The micro controller 1303 is coupled to sensors 1305 and to energy sources 1307 through a bus 1306. The sensors 1305 may be electrical skin contact sensors (such as, e.g., electrodes 503d and 503e), or pressure sensors which detect a pressure above or below atmospheric pressure, and/or skin temperature sensors, and/or skin color sensors and/or a combination of these (and other) sensors. The energy sources 1307 may be multiple light sources and/or radio frequency electrical electrodes and/or other types of energy sources described herein and/or a combination of these sources. The device 1301 also includes a cable 1309, which is similar to cable 905 (attached to handle 906) of the device 900 of FIG. 9. The cable provides power to the handheld from a separate power supply (which may be bulky and thus not practical to hold in a hand), and the cable also provides vacuum and air pressures from a separate (potentially bulky) vacuum pump and air pump. The device 900 also includes manual controls such as a pneumatic adjustment control 903 (allowing the vacuum to be adjusted) and a power adjustment control 904 (allowing the power of a treatment to be adjusted manually by an operator). The device 900 also includes a disposable tip 902 which may be a detachable membrane such as membrane 301 which attaches to the treatment face of the body of the device 900.

The micro controller 1303 may be programmed to operate the device in one or more of the methods described herein. For example, the micro controller 1303 may receive signals from a skin color sensor 1305 which causes the micro controller 1303 to automatically adjust (without any user input and/or intervention) the power level of the energy sources; the handheld display can then be updated to show that the power level has been changed (and this may be noticed by the operator who can override the changed power setting). The skin color sensor(s) may also be used to detect the return of blood pushed away by an object protruding within the recess of the device; upon detecting this change in skin color from signals from the skin color sensor, the micro controller shuts off the power to the energy sources in one embodiment of the invention, and another cycle (e.g., as shown in FIG. 2a) may be performed to continue the treatment at the same treatment site. The micro controller 1303 may also receive signals from a skin temperature sensor 1305 which causes the micro controller 1303 to automatically adjust (without any user input and/or intervention) the power level of the energy sources; if, for example, the skin temperature becomes too hot, the micro controller may completely turn off the power to the energy sources in order to protect the patient's skin.

The micro controller 1303 may also receive signals from a pressure sensor which indicates that the device has been presses against the skin at a desired treatment site, thereby creating a seal between the device and the skin; the resulting pressure change (due to this seal) in the recess is detected, and the micro controller begins, automatically, a desired treatment (at either predetermined settings previously entered by an operator and/or automatically based on skin color sensor signals and settings previously entered by an operator). In this case, the micro controller may cause an object (e.g., object 401) to press against the skin and cause the vacuum to be generated and then apply energy from the energy sources before the blood returns to the treatment. Pressing the object against the skin and generating a vacuum may be concurrent (completely overlapped in time) and/or partially overlapping in time and/or sequential with no overlap in time. The micro controller 1303 may use a timer to determine when the blood returns (to a normal concentration level after having been pushed away) and/or may use signals from a skin color sensor; the timer may be started upon pushing with the protruding object, and the elapsed time may be counted. In this way, the micro controller can assure that the energy is applied in the time period (e.g., 100 m sec) before the blood returns to a normal concentration. If the object which pushes the blood away is moveable, the micro controller may control its movement.

FIGS. 14A-F are graphical process flows of a device to treat biological external tissue using a liquid and/or other material to cool the biological external tissue before and/or during application of an energy, according to one embodiment.

Figure 14A:
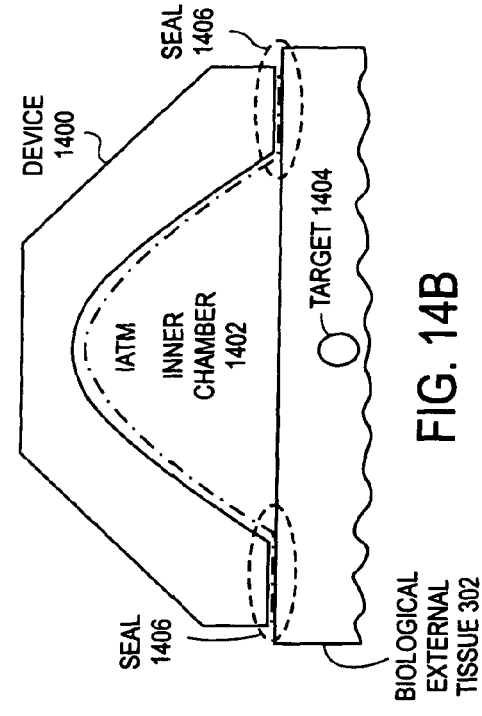
FIG. 14A-F are graphical process flows of a device to treat biological external tissue using a liquid and/or other material to cool the biological external tissue before and/or during application of an energy, according to one embodiment.

First, in FIG. 14A, a device 1400 having an inner chamber 1402 may be applied to the biological external tissue 302. The pressure within the inner chamber 1402 of the biological external tissue is 1 ATM (e.g., atmospheric pressure) in FIG. 14A. A target 1404 (e.g., a unwanted hair, a wrinkle, a skin blemishes, a tattoo, a vascular and pigmented lesion, etc.) may reside within the biological external tissue 302 directly below the inner chamber 1402. The target 1404 may be eradicated, reduced, and/or treated by the device 1400.

In one embodiment, at atmospheric pressure, a contact cooling of the biological external tissue 302 may be performed prior to or after placing the device 1400 on the biological external tissue 302 in FIG. 14A. The contact cooling may be performed by placing a cold, optically transparent element (not shown) on the biological external tissue 302 prior to, during and after treatment (e.g., application of energy as later will be described in FIG. 14E). The optically transparent element may cool the area to be treated (e.g., the biological external tissue 302 directly below the inner chamber 1402) to a temperature below normal body temperature (e.g. the normal body temperature of a human being, and/or other living being having biological external tissue 302). The temperature rise of the pre-cooled area of the biological external tissue 302 to a level where the biological external tissue 302 burns is more than for a non pre-cooled area. For example, if the goal is to always maintain a treated area of the biological external tissue 302 below 60 C, the temperature of the treated area must rise from 33 C to 60 C or 27 C if not pre-cooled. If pre-cooled to 10 C, the area must rise 50 C (e.g., from 10 C to 60 C). During the application of the energy, (e.g., as will be described in FIG. 14E), the optically transparent element may remove heat from the treated area of the biological external tissue 302 faster than it is removed without the cooling, thereby providing the biological external tissue 302 with additional protection from the heat caused by the treatment.

In another embodiment, at atmospheric pressure, a cryogen spray (e.g., a liquid, such as liquid nitrogen, that boils at a temperature below about 110 K (−160° C.) and is used to obtain very low temperatures) may be used to pre-cool the biological external tissue 302 prior to placing the device 1400 on the biological external tissue 302 in FIG. 14A. The cryogen spray (not shown) may cool an area of biological external tissue 302 to be treated by rapid evaporation of the cryogen. As with the contact cooling, temperature rise of the cryogen pre-cooled area to a level where the biological external tissue 302 burns are greater than for a non pre-cooled area. Furthermore, as with contact cooling, the cooling effect of the cryogen spray during the application of the energy, (e.g., as will be described in FIG. 14E) provides some additional protection because the cryogen pre-cooled area may remove heat from the treated area of the biological external tissue 302 faster than it is removed without the pre-cooling.

Figure 14B:
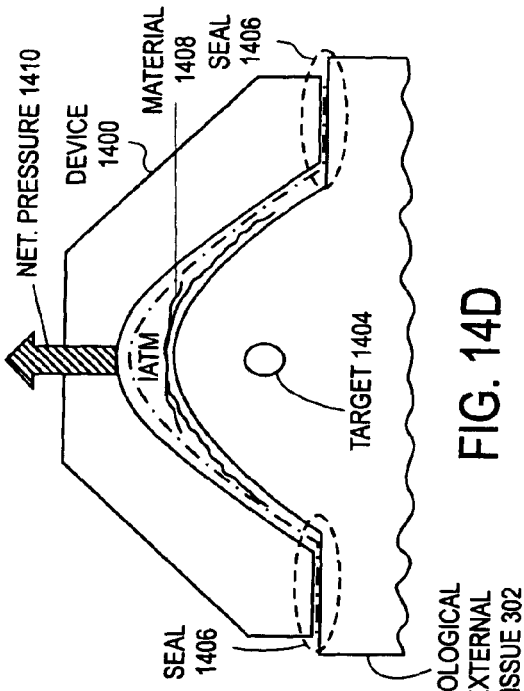
Figure 24:
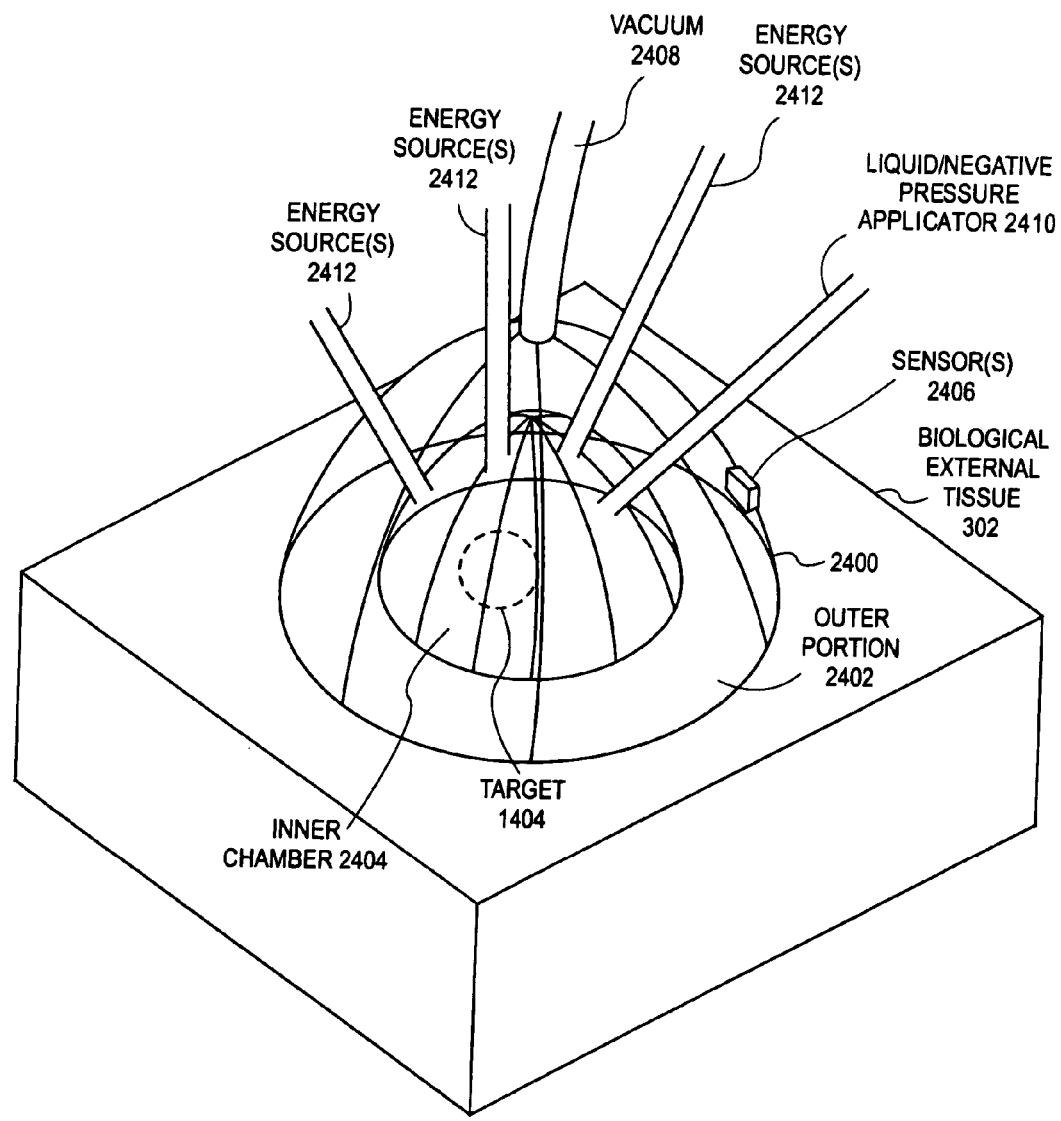
FIG. 24 is a three-dimensional view of a device having an inner chamber and an outer portion to treat biological external tissue according to one embodiment.

Next, in FIG. 14B, a seal 1406, (e.g., a vacuum seal), is formed between the device 1400 and the biological external tissue 302. In one embodiment, as shown in FIG. 24, the seal 1406 may be formed within an outer portion 2402 of a device 2400. In yet another embodiment, as shown in FIG. 11, the seal is generated at the periphery of the device 1100 through the pressure conduits 1004 and 1003. Referring back to FIG. 14B, the seal 1406 may prevent the device 1400 from shifting above the target 1404 during an application of negative pressure, (as described in FIGS. 2a, 2b, and 2c, and as will be further discussed in FIG. 14D), and/or shifting during the application of an of an energy (as described in FIGS. 2a, 2b, and 2c, and as will be further discussed in FIG. 14E).

Figure 14C:
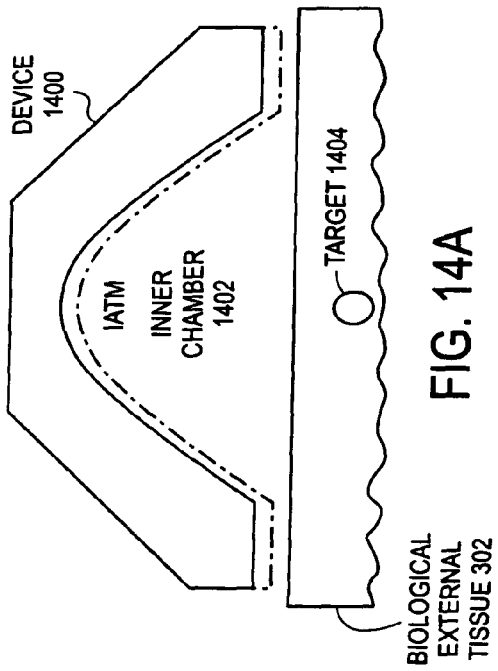

Then, in FIG. 14C, a material 1408, (e.g., a liquid such as water and/or ethyl alcohol, and/or other solid, liquid and/or gas substance having desired properties), is applied to the biological external tissue 302. In one embodiment, the material 1408 is applied through a conduit 1502 as shown on the device 1500 in FIG. 15. The material 1408 of FIG. 14C is effective, (e.g., as a cooling material), at pressures below atmospheric pressure, and is different than the contact cooling embodiment and the cryogen cooling embodiment described in FIG. 14A. As described with reference to FIG. 14A, the contact cooling embodiment and the cryogen cooling embodiment work effectively primarily at atmospheric pressure. As such, contact cooling and cryogen spray may not be effective at pressures below atmospheric pressure (e.g., one atmosphere). Materials that provide little evaporative cooling at atmospheric pressure may provide significant evaporative cooling at pressures less than one atmosphere. Water, for example, provides little evaporative cooling at atmospheric pressure, but "boils" at 60 C in one third of an atmosphere and can provide significant evaporative cooling at one third of an atmosphere. These materials may be the material 1408 that is applied to the biological external tissue in the operation shown in FIG. 14C.

There are other materials, substances, and liquids that could be used effectively for the material 1408. An important criterion is that the material 1408, at a desired temperature, have a vapor pressure equal to or higher than the pressure inside the device 1400 during treatment, (.e.g., application of energy 1414 as described in FIG. 14E). Many alcohols meet this criterion. Ethyl alcohol has a vapor pressure of −15 PSI at 57 C. Its heat of vaporization is 854 Joules per gram which is less than water's 2450 Joules per gram. Nevertheless, ethyl alcohol may also provide elevated cooling at 55 C as it carries off excess heat by vaporizing. In one embodiment, the material 1408 is applied prior to treatment. In another embodiment, the material 1408 is applied as a spray, wiped out using a sponge and/or other object and/or in any other suitable manner.

Figure 14D:
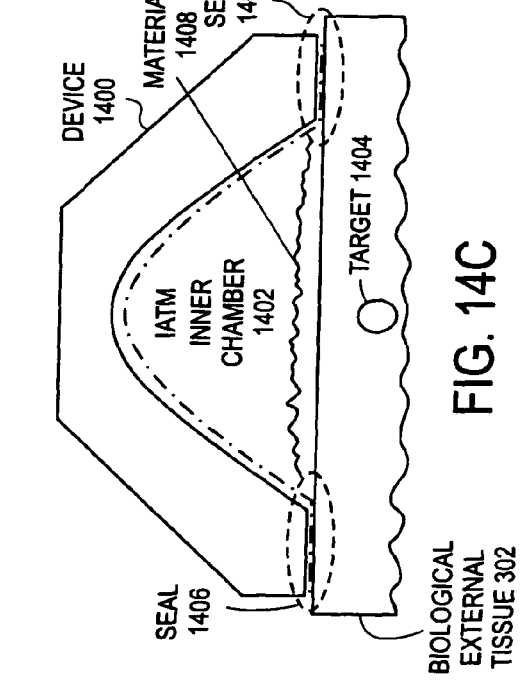

Next, in FIG. 14D a negative pressure 1410 is applied to the device 1400. In one embodiment, as shown in FIG. 11, the negative pressure is applied through the pressure conduit 1103. The negative pressure 1410 may bring a portion of the biological external tissue 302 having the target 1404 upward within the inner chamber 1402 as illustrated in FIG. 14D. In another embodiment, the negative pressure 1410 is applied after following the process described in FIGS. 2a, 2b, and 2c. Illustrated in FIG. 14D, the negative pressure 1410 may reduce the pressure within the inner chamber 1402 below 1 ATM.

Figure 14E:
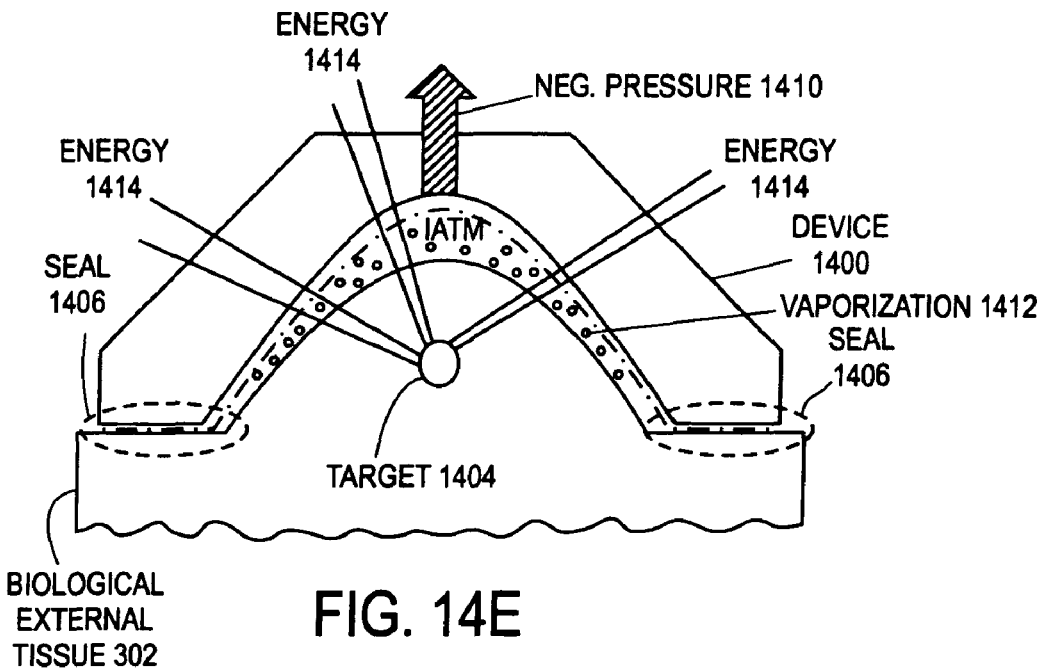

Then, in FIG. 14E, the reduction of pressure within the inner chamber 1402 as described in FIG. 14D may cause the material 1408 to change physical state (e.g., from a liquid to a gas). When the material 1408 changes from a liquid to a gas, it may undergo a process called vaporization 1412 as shown in FIG. 14E.

The quantity of heat required to change the physical state of the material 1408 from a liquid to a gas through vaporization 1412 is called a heat of vaporization. For example, if the material 1408 is water, the heat of vaporization of water is 2450 Joules per gram. Prior to vaporization, the quantity of heat required to raise one gram of water one degree centigrade is called its specific heat. The specific heat of water is 4.184 Joules/gm. As liquid water is heated, every 4.184 Joules of energy that is applied to every gram of water heats that gram one degree centigrade. Assuming no heat losses, if 126 Joules of energy are applied to one gram of water, it will heat it from 30 degrees Centigrade to 60 degrees Centigrade. Adding another 168 Joules to this one gram of water will heat it to its "boiling point" at 100 degrees Centigrade.

The "boiling point" of water at atmospheric pressure is 100 degrees Centigrade. At the boiling point, it will require 2450 Joules before its temperature starts to rise above 100 degrees Centigrade. This is 35 times more energy than was needed to heat this one gram of water from 30 C to 100° C. At this time, this one gram of water will no longer be a liquid. It will be a gas.

At atmospheric pressure, the boiling point of water is 100 degrees Centigrade. At pressures less than atmospheric pressure (e.g., less than one atmosphere), the "boiling point" of water is reduced. At a pressure of −12 psi, the "boiling point" of water is 60 C. As in the previous example, 126 Joules of energy is required to heat one gram of water from 30 Centigrade to 60 Centigrade. The temperature would then stop rising until 2450 Joules is applied to this one gram of water. If this water is on the biological external tissue 302 (e.g., skin), it may provide strong protection for the biological external tissue 302 rising above 60 Centigrade. Since it may require several seconds for biological external tissue (e.g., human skin) to burn at 60 C, placing water on the skin in a reduced atmosphere may prevent burning.

Figure 1A:
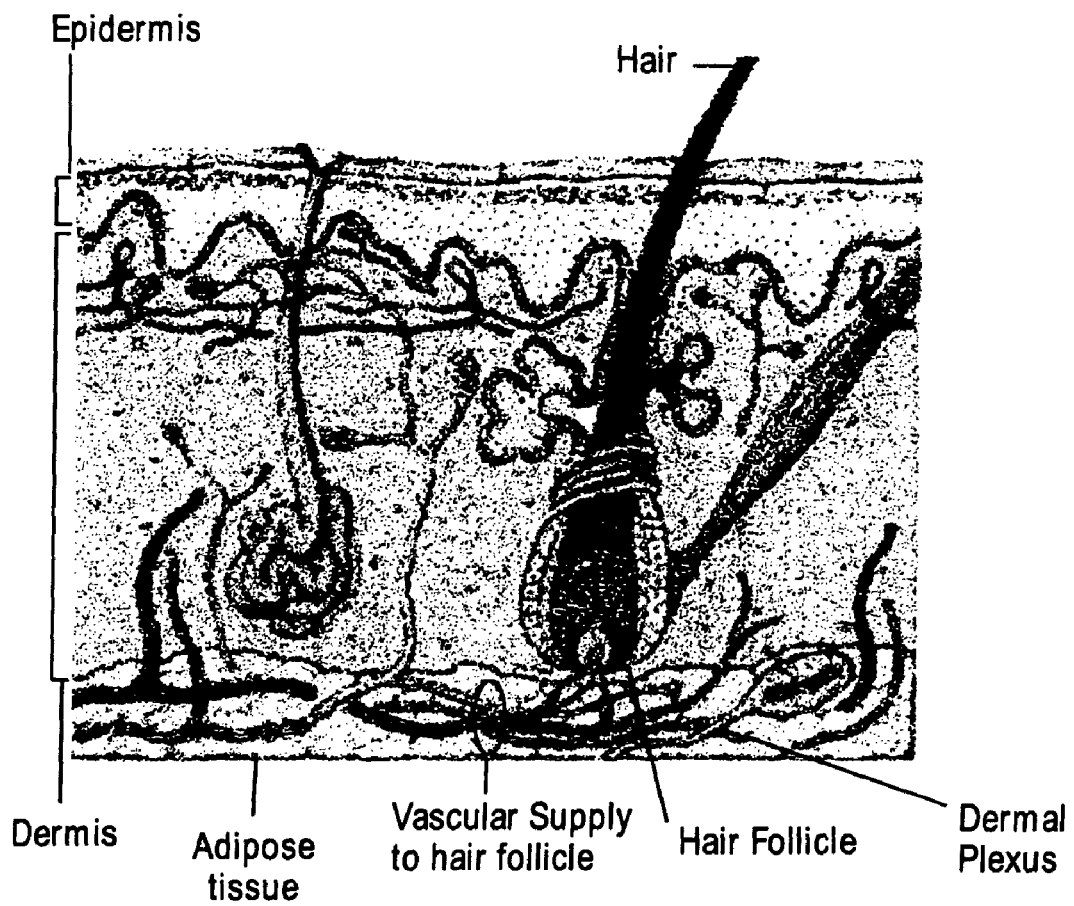
FIG. 1a is a diagram showing the various layers of the skin and potential targets for photo therapy and/or electrical therapy, according to one embodiment.
Figure 1B:
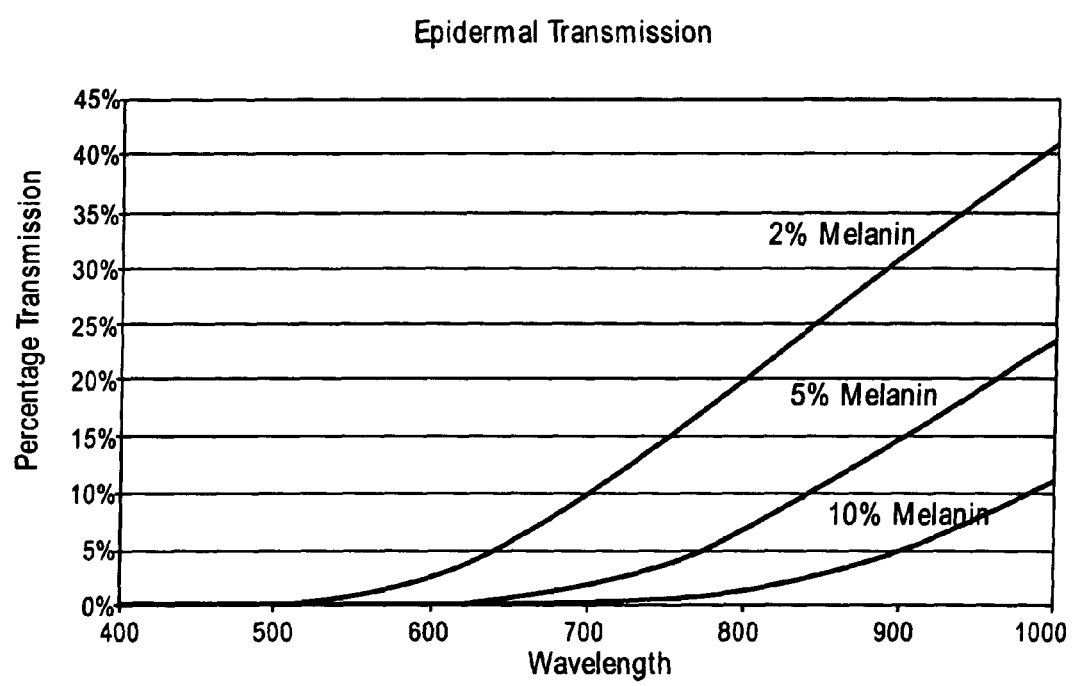
FIG. 1b is a chart showing the percentage of incident energy transmitted through the epidermis for three different skin types, according to one embodiment.
Figure 1C:
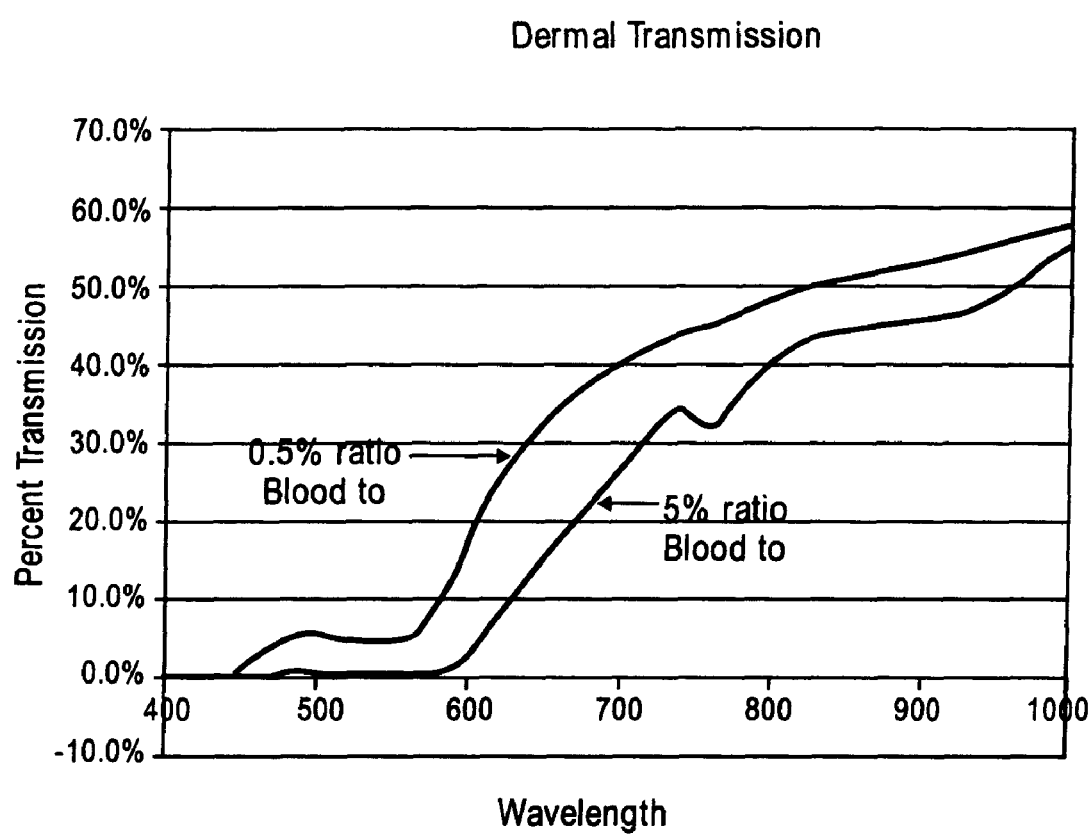
FIG. 1c is a chart showing the percentage of incident energy transmitted through the dermal plexus for two different levels of blood concentration (shown as ratios of blood to the rest of the tissue in a given volume), according to one embodiment.

Referring back to FIG. 14E, an energy 1414 may also be applied to the biological external tissue 302 using the device 1400. In one embodiment, the energy 1414 is the same energy as described previously in FIGS. 2a, 2b, and 2c in operation 204. Specifically, the energy 1414 may be incoherent light, coherent light, radio frequency, and/or ultrasound, according to various embodiments of the invention. The energy 1414 may be a combination of multiple energies such as a radio frequency and a coherent light in some embodiments of the invention. Applying the energy 1414 may destroy and/or alter a targeted chromophore (e.g., a target 1404) or other target in the dermis and/or epidermis without injuring and/or burning the surrounding epidermis and dermis (e.g., as shown in FIG. 1a) in the biological external tissue 302.

Figure 14F:
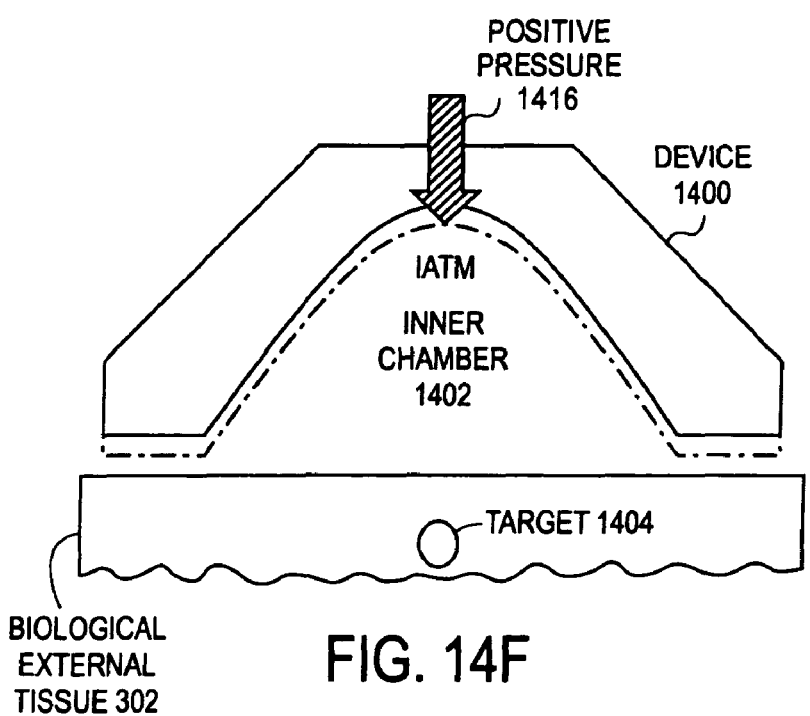

Lastly, in FIG. 14F, the device 1400 may be removed from the biological external tissue 302 by applying a positive pressure 1416 to the biological external tissue 302 using the device 1400. The portion of the biological external tissue 302 having the target 1404 (as described in FIG. 14D) may be pushed outside the inner chamber 1402 by the positive pressure 1416 as illustrated in FIG. 14F. In one embodiment, the positive pressure is applied through the pressure conduits 1004 and 1003 as described in FIG. 10. In another embodiment, the pressure within the inner chamber 1402 of the biological external tissue returns to 1 ATM in FIG. 14F, from a pressure below 1 ATM in FIGS. 14D and 14E because the device 1400 is lifted from the biological external tissue 302. The seal 1406 between the device 1400 and the biological external tissue 302 as described in FIG. 14B may be eliminated in the operation shown in FIG. 14F. It should be noted that the target 1404 may be completely eliminated, (e.g., by the application of the energy 1414), by the time the operation as shown in FIG. 14F is performed in one embodiment.

Figure 15:
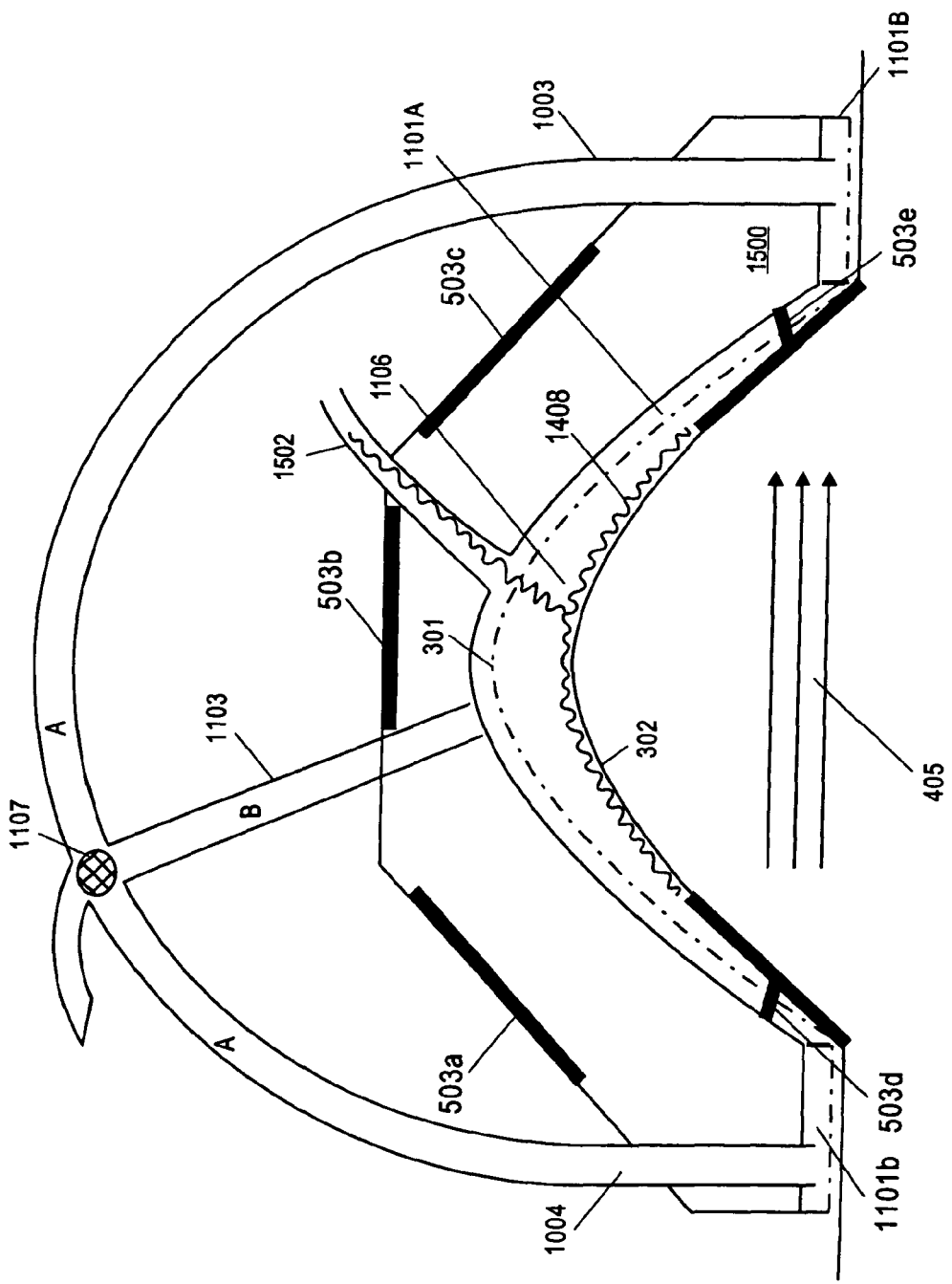
FIG. 15 is a cross-sectional view of a device 1500 having a body that is applied to biological external tissue 302, the device 1500 having multiple vacuum chambers and a material conduit thru which a material is applied to the biological external tissue, according to one embodiment.

FIG. 15 is a cross-sectional view of a device 1500 having a body that is applied to biological external tissue 302, the device 1500 having multiple vacuum chambers (conduits 1004, 1103, 1003 as previously described in FIG. 11) and a material conduit 1502 thru which the material 1408 is applied to the biological external tissue 302, according to one embodiment. The device 1500 in FIG. 15 is similar to the device 1100 shown in FIG. 11, except the device 1500 includes the material conduit 1502. In one embodiment, the material 1408 is applied through the conduit 1502 as shown on the device 1500 in FIG. 15. In another embodiment, the material 1408 is water and/or ethyl alcohol.

Figure 16:
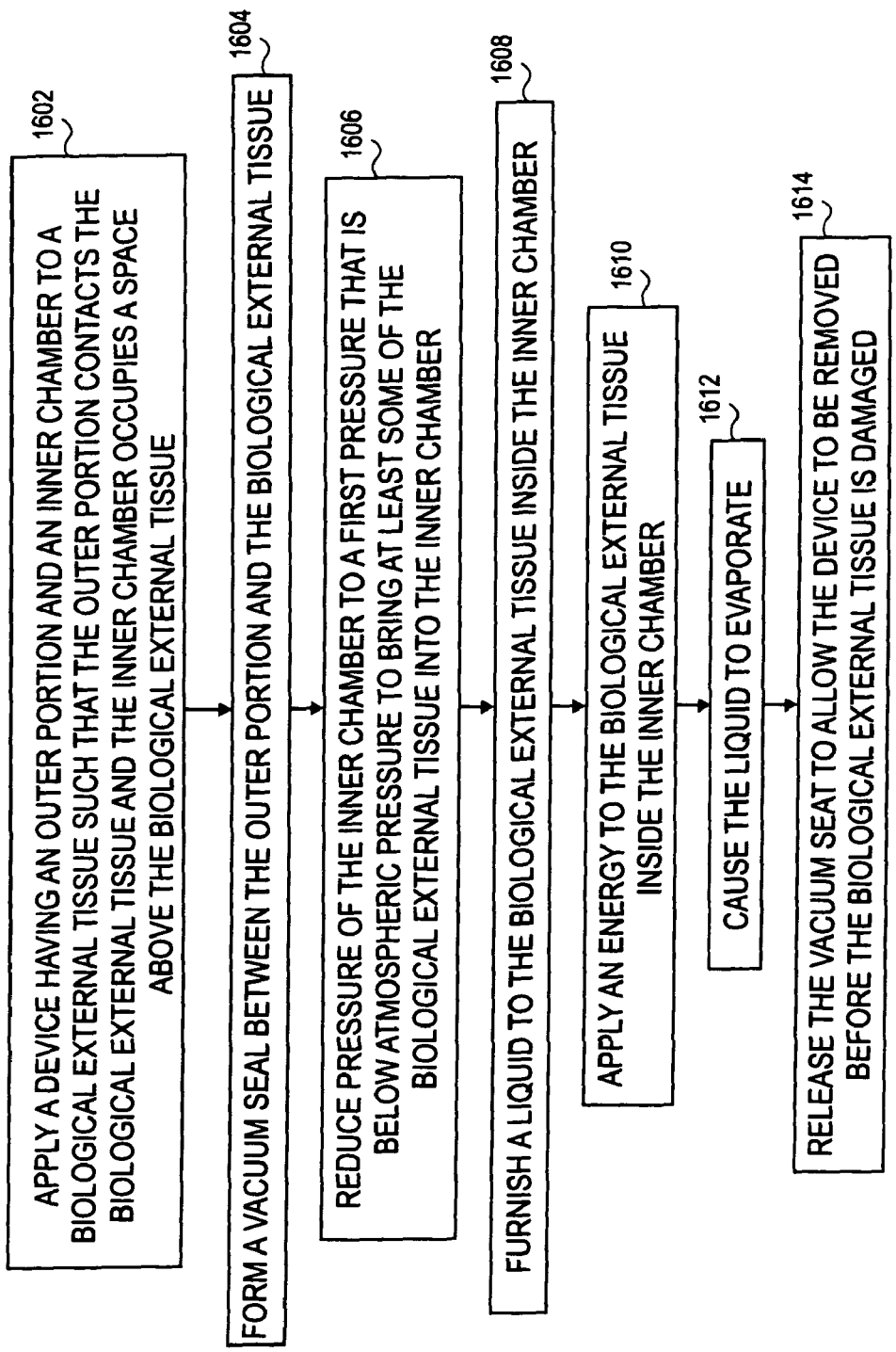
FIG. 16 is an operation flow of reducing pressure of an inner chamber and applying a material to the biological external tissue, according to one embodiment.

FIG. 16 is an operation flow of a method of reducing pressure of an inner chamber and applying a material to the biological external tissue, according to one embodiment. In operation 1602, a device (e.g., the device 2400 as illustrated in FIG. 24, the device 1400 as illustrated in FIG. 14, and/or the devices illustrated in FIGS. 3-12, etc.) having an outer portion 2402 (e.g., as illustrated in FIG. 24) and an inner chamber 2404 (as illustrated in FIG. 24) is applied to the biological external tissue 302 (as illustrated in FIG. 24) such that the outer portion 2402 contacts the biological external tissue 302 and the inner chamber 2404 occupies a space above the biological external tissue 302.

In operation 1604 of FIG. 16, a vacuum seal (e.g., a seal 1406 as described in FIG. 14B) is formed between the outer portion 2402 and the biological external tissue 302. In operation 1606, the pressure of the inner chamber 2404 is reduced to a first pressure that is below atmospheric pressure (e.g., as shown in FIG. 14D) to bring at least some of the biological external tissue 302 into the inner chamber 2404 (e.g., and/or alternatively inner chamber 1402 as illustrated in FIGS. 14A-F).

In operation 1608, a liquid (e.g., water and/or other material 1408 as illustrated in FIG. 14C) is furnished to the biological external tissue 312 inside the inner chamber 2404 (as shown in FIG. 24). In operation 1610, an energy (e.g., the energy 1414 as shown in FIG. 14E) is applied to the biological external tissue 302 inside the inner chamber 2404. In operation 1612, the liquid (e.g., material 1408) evaporates (e.g., through vaporization 1412 as shown in FIG. 14E and/or through other means). In operation 1614, the vacuum seal (e.g., seal 1406 in FIG. 14B) is released to allow the device (e.g., the device 2400 of FIG. 24) to be released before the biological external tissue 302 is damaged (e.g., burned). It will be appreciated that other embodiments of the implementation shown in FIG. 16 may have a different sequence of operations. For example, operation 1608 may precede operation 1606.

Figure 17:
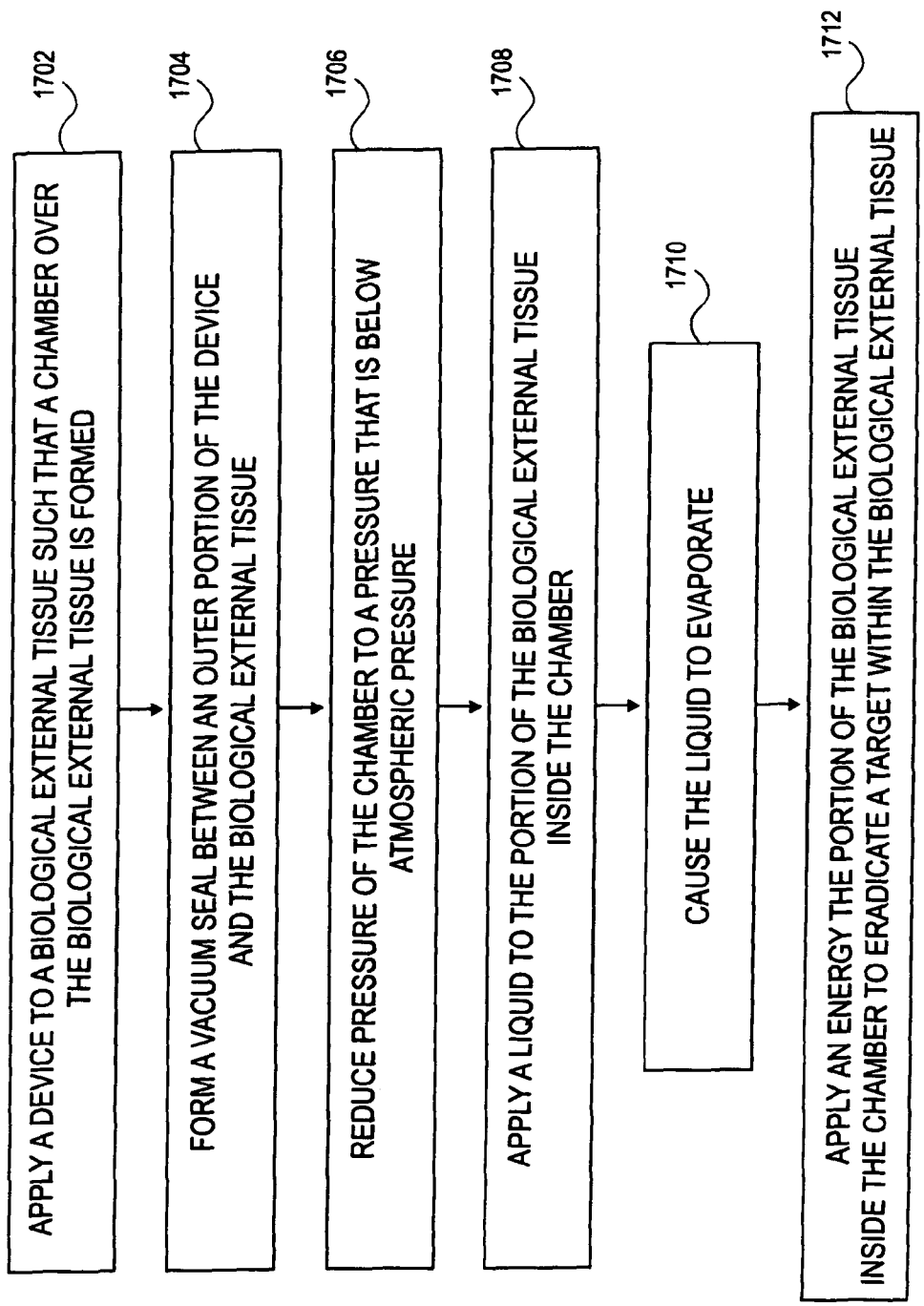
FIG. 17 is an operation flow of forming a vacuum seal between a device and a biological external tissue, and applying a material to the biological external tissue within a chamber formed above the biological external tissue, according to one embodiment.

FIG. 17 is another example of an embodiment of the invention. In operation 1702, a device (e.g., such as cut-away view 2300 in FIG. 23 of the device 1400 in FIG. 14A) having a cavity 2308 is applied to a biological external tissue 302 (e.g., as illustrated in FIGS. 3-24), such that a chamber (e.g., the inner chamber 1402 as illustrated in FIG. 14A) over the biological external tissue 302 is formed. In operation 1704, a vacuum seal (e.g., a seal 1406 as illustrated in FIG. 14B) of an outer cut-away 2310 (e.g., the outer cut-away 2310 in FIG. 23 may be a cross-sectional view of the outer portion 2402 in FIG. 24) and the biological external tissue 302 is formed. In operation 1706, the pressure of the chamber (e.g., the inner chamber 1402 as illustrated in FIG. 14A) is reduced to a pressure that is below atmospheric pressure to bring at least a portion of the biological external tissue 302 into the chamber. In operation 1708, a liquid (e.g., water and/or other material 1408) is applied to the portion of the biological external tissue 302 inside the chamber (e.g., the inner chamber 1402 as illustrated in FIG. 14A). In operation 1710, the liquid evaporates (e.g., through vaporization 1412 as shown in FIG. 14E and/or through other means). In operation 1712, an energy (e.g., the energy 1414 as shown in FIG. 14E) is applied to the portion of the biological external tissue 302 inside the chamber to eradicate a target (e.g., the target 1404 in FIG. 14A) within the biological external tissue 302. It will be appreciated that other implementations of the method of FIG. 17 may use a different sequence of operations.

Figure 18:
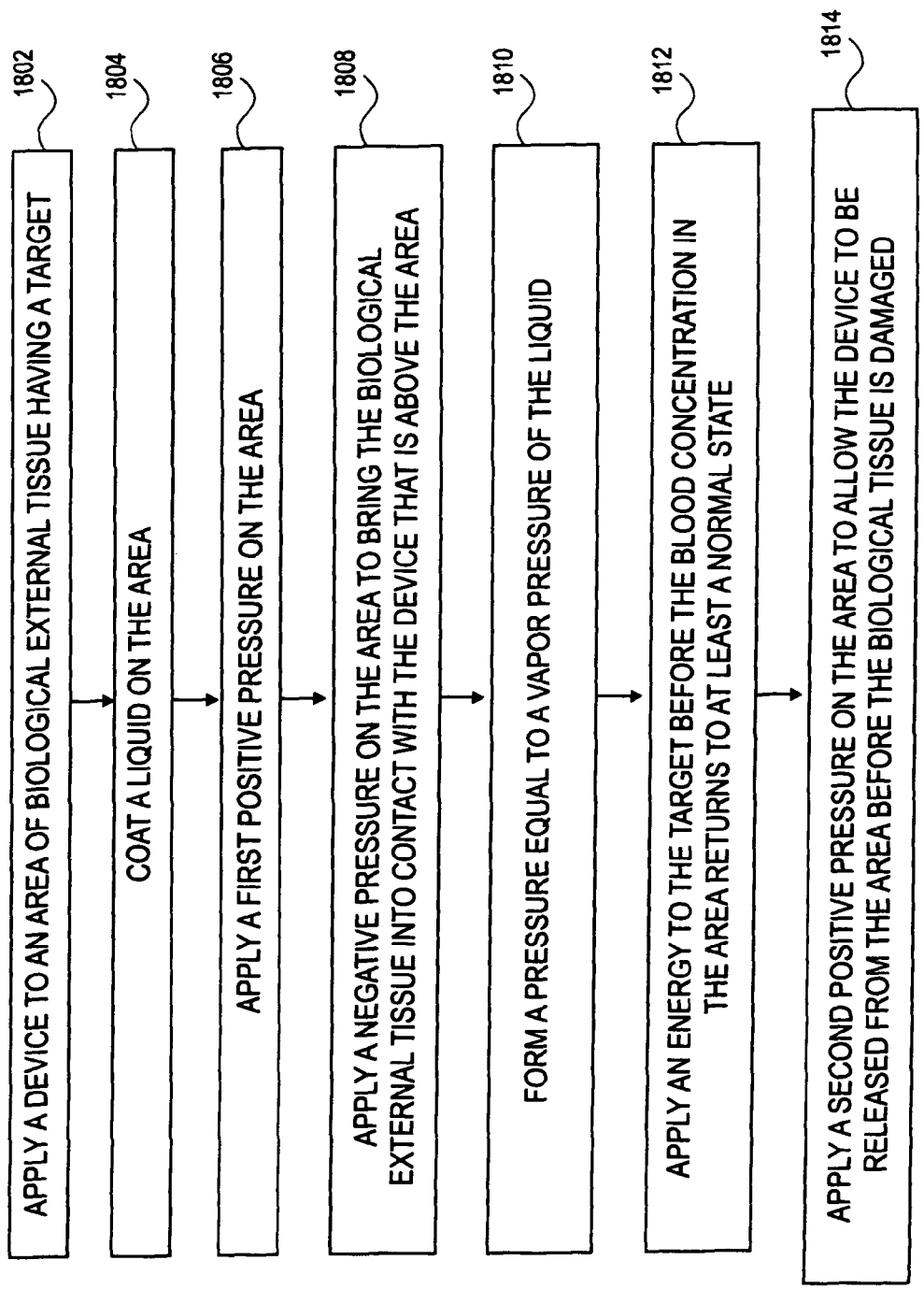
FIG. 18 is an operation flow of coating a liquid on an area of biological external tissue, forming a pressure equal to or lower than a vapor pressure of the liquid, and applying an energy to a target before the blood concentration in the biological external tissue returns to at least a normal state, according to one embodiment.
Figure 23:
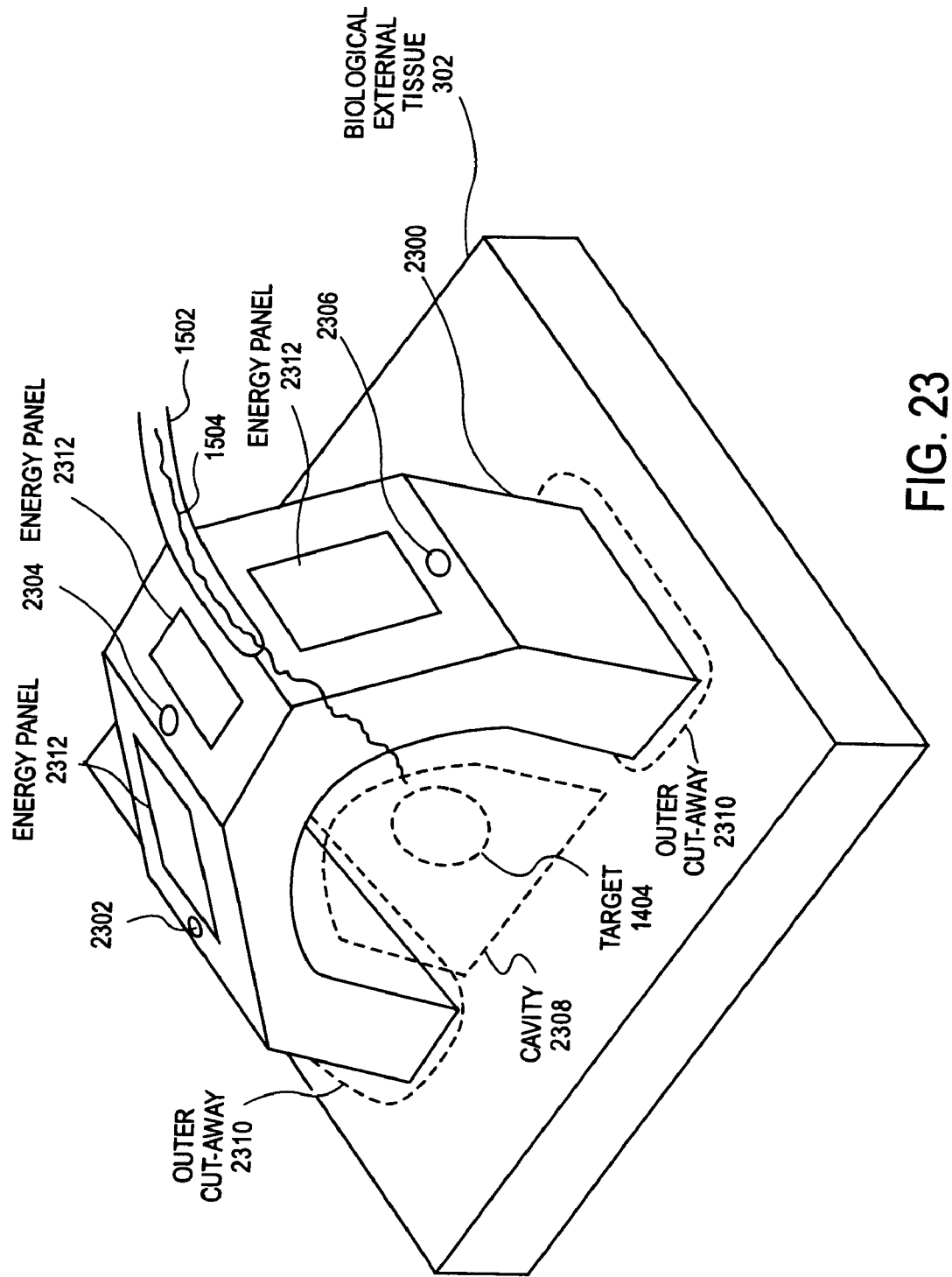
FIG. 23 is a three-dimensional, cut-away view of a device to treat biological external tissue according to one embodiment.

FIG. 18 is an operation flow of a method of coating a liquid on an area of biological external tissue, forming a pressure equal to or lower than a vapor pressure of the liquid, and applying an energy to a target before the blood concentration in the biological external tissue returns to at least a normal state, according to one embodiment. In operation 1802, a device (e.g., a cut-away view 2300 as illustrated in FIG. 23 and/or a device 2400 as illustrated in FIG. 24) is applied to an area of biological external tissue 302 having a target 1404. In operation 1804, a liquid (e.g., water and/or other material 1408) is coated on the area of biological external tissue 302 to be treated. In operation 1806, a first positive pressure (e.g., as described in FIG. 2c in operation 202c) is applied on the area. In operation 1808, a negative pressure (e.g., as described in FIG. 2c in operation 203, and as illustrated in FIG. 14D) is applied on the area to bring the biological external tissue 302 into contact with the device that is above the area. In operation 1810, a pressure is formed equal to a vapor pressure of the liquid (e.g., to vaporize the liquid as illustrated in vaporization 1412 of FIG. 14E). In operation 1812, an energy is applied to the target 1404 before the blood concentration in the area returns to at least a normal state. In operation 1814, a second positive pressure is applied on the area to allow the device to be released from the area before the biological external tissue 302 is damaged (e.g., as described in FIG. 2c in operation 202d and as illustrated in FIG. 14F). It will be appreciated that other implementations of the method of FIG. 18 may use a different sequence of operations.

Figure 19:
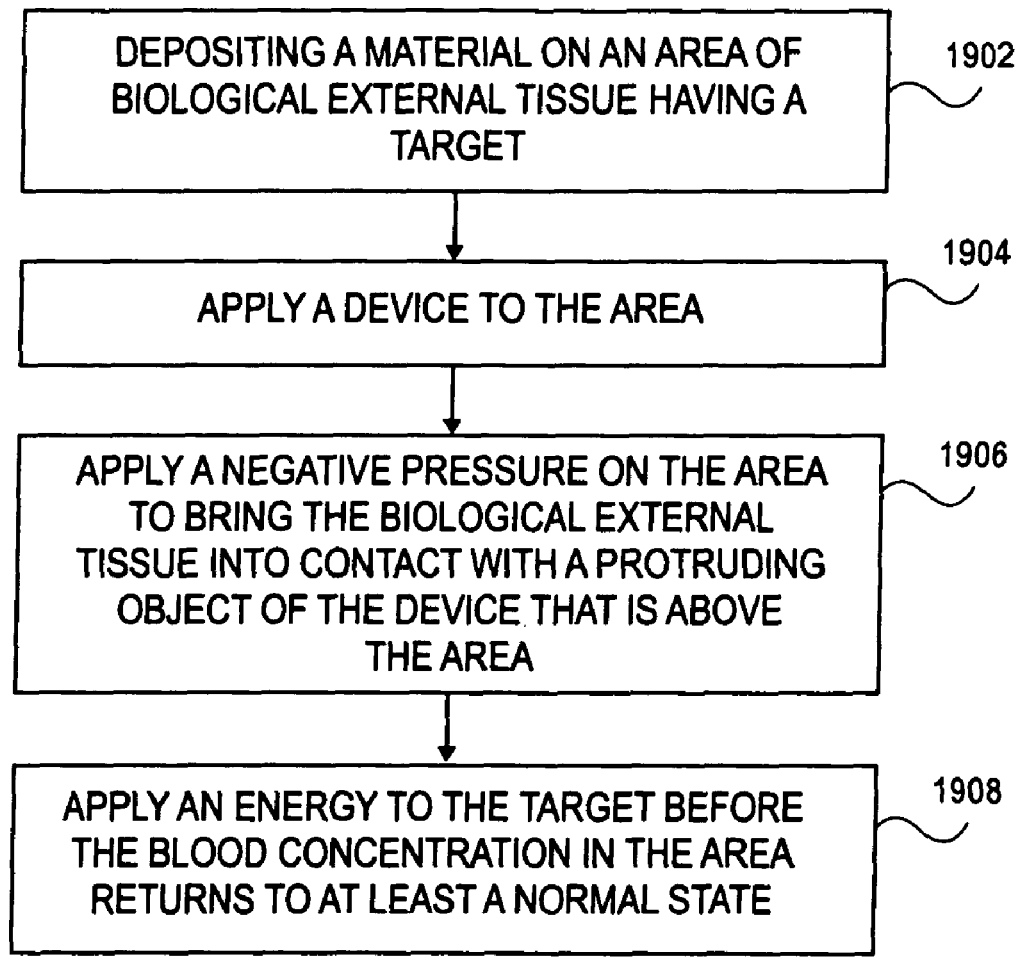
FIG. 19 is an operation flow of depositing a material on an area of a biological external tissue having a target, applying a device to the area, and bringing the biological external tissue into contact with a protruding object of the device that is above the area.

FIG. 19 is an exemplary embodiment of a method which includes depositing a material on an area of a biological external tissue having a target, applying a device to the area, and bringing the biological external tissue into contact with a protruding object of the device that is above the area. In operation 1902, a material 1408 (as illustrated in FIG. 14C) is deposited on an area of biological external tissue 302 having a target 1404. In operation 1904, a device (e.g., a device 500 as illustrated in FIG. 5 and/or a device 1400 as illustrated in FIG. 14A-F) is applied to the area. In operation 1906, a negative pressure is applied on the area to bring the biological external tissue into contact with a protruding object (e.g., object 401 in FIG. 4 and FIG. 5) of the device that is above the area (e.g., as described in FIG. 5). In operation 1908, an energy (e.g., an energy 1414) is applied to the target 1404 before the blood concentration in the area of biological external tissue 302 returns to at least a normal state. It will be appreciated that other implementations of the method of FIG. 11 may use a different sequence of operations.

Figure 20:
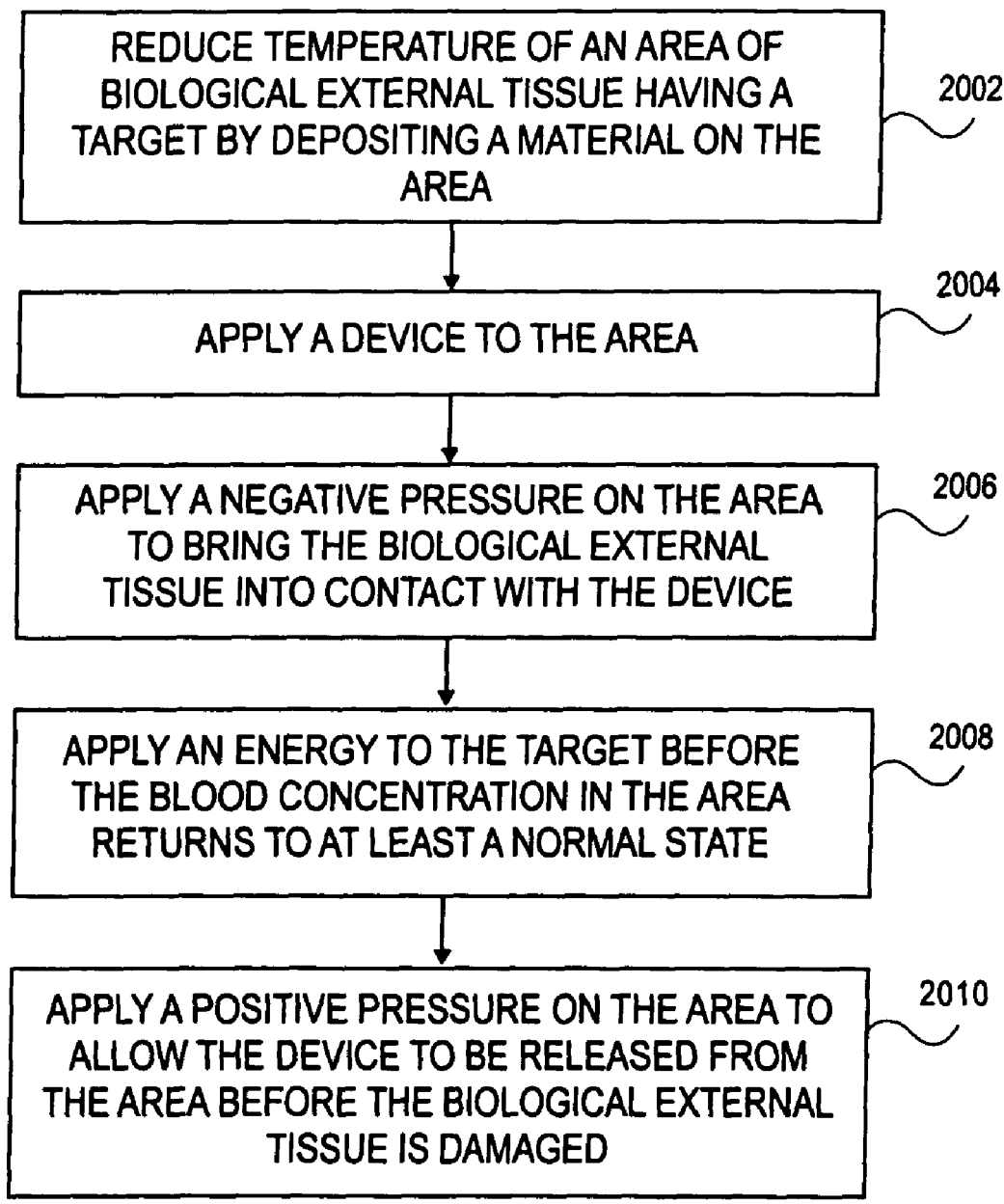
FIG. 20 is an operation flow of reducing temperature of an area of a biological external tissue having a target by depositing a material on the area, applying a negative pressure to bring the biological external tissue into contact with the device, and applying an energy to the target before the blood concentration in the area returns to at least a normal state, according to one embodiment.

FIG. 20 is another exemplary embodiment of a method which includes reducing temperature of an area of a biological external tissue having a target by depositing a material on the area, applying a negative pressure to bring the biological external tissue closer to and/or into contact with the device, and applying an energy to the target before the blood concentration in the area returns to at least a normal state, according to one embodiment. In operation 2002, temperature of an area of biological external tissue 302 having a target 1404 is reduced by depositing a material 1408 on the area of biological external tissue 302. In operation 2004, a device (e.g., a device 1400 of FIG. 14A-F) is applied to the area. In operation 2006, a negative pressure (e.g., negative pressure 1410 in FIG. 14D) is applied on the area to bring the biological external tissue closer to and/or into contact with the device (e.g., as described and illustrated in FIG. 14D). In operation 2008, an energy (e.g., an energy 1414) is applied to the target 1404 before the blood concentration in the area returns to at least a normal state. In operation 2010, a positive pressure (e.g., positive pressure 1416 in FIG. 14F) is applied on the area to allow the device to be released from the area before the biological external tissue 302 is damaged (e.g., as described and illustrated in FIG. 14F). It will be appreciated that other implementations of the method of FIG. 20 may use a different sequence of operations.

Figure 21:
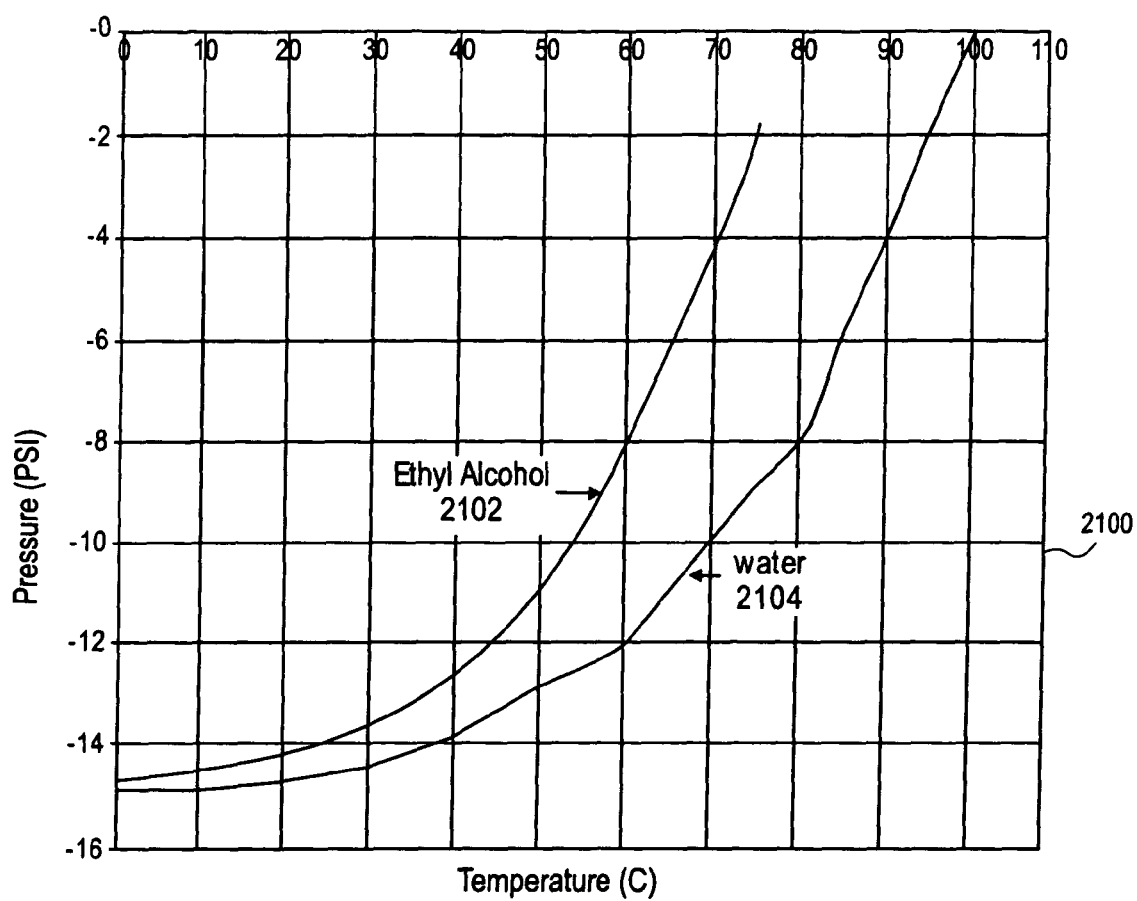
FIG. 21 is a graph illustrating the vaporization pressure in PSI of ethyl alcohol and water as a function of temperature in Celsius, according to one embodiment.

FIG. 21 is a graph illustrating the vaporization pressure in PSI of ethyl alcohol and water as a function of temperature in Celsius, according to one embodiment. There are two curves illustrated in chart 2100 in FIG. 21, one curve 2102 for ethyl alcohol, and another curve 2104 for water. The ethyl alcohol curve 2102 shows various vaporization pressures as a function of temperature. For example, at a temperature of 60 degrees Celsius, the vaporization pressure of ethyl alcohol is approximately −8 PSI. As another example, at a temperature of 60 degrees Celsius, the vaporization pressure for water is slightly below −12 PSI.

Figure 22:
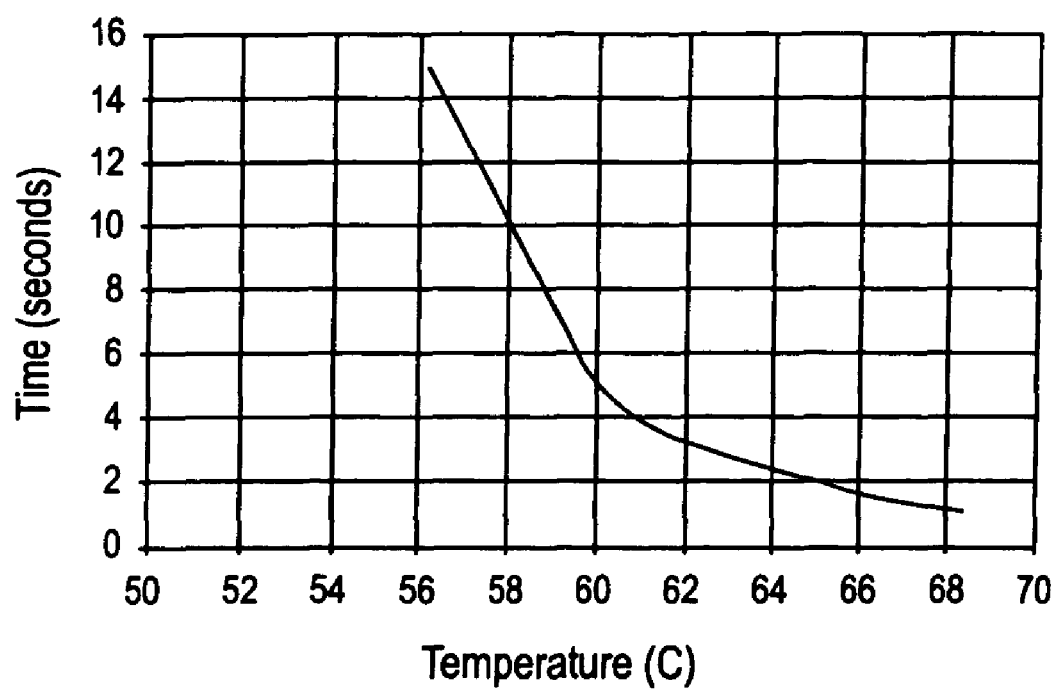
FIG. 22 is a graph illustrating the time in seconds to burn biological external tissue, according to one embodiment.

FIG. 22 is a graph illustrating the time in seconds to burn biological external tissue, according to one embodiment. The single curve in FIG. 22 illustrates an exponential decline in the number of seconds it takes to burn biological external tissue (e.g., human skin) as temperature increases. For example, at a temperature of 58 degrees Celsius, it takes slightly under 10 seconds to burn skin, whereas at a temperature of 64 degrees Celsius, it takes only 2 seconds to burn skin.

FIG. 23 is a three-dimensional, cut-away view of a device to treat biological external tissue according to one embodiment. Portions of FIG. 23 have been previously described in detail in conjunction with FIG. 17. FIG. 23 illustrates a cut-away view 2300 (e.g., the cut-away view 2300 may be a three-dimensional cross-sectional view of a device 2400 as illustrated in FIG. 24) having a cavity 2308 and an outer cut-away 2310 for treating the biological external tissue 302 having a target 1404.

In addition, the cut-away view 2300 in FIG. 23 also includes a port 2302, a port 2304, and port 2306. While three ports (2302, 2304, and 2304) are illustrated, other embodiments may have any number of ports or no ports at all. The ports 2302 and 2306 may be used to pressure conduits 1004 and 1003 as illustrated in FIG. 11 to connect to the cut-away view 2300 in one embodiment (e.g., to allow a seal 1406 to be formed as illustrated in FIG. 14D). The port 2304 may be used to allow the conduit 1103 (as illustrated in FIG. 11) to connect to the cut-away view 2300 in another embodiment (e.g., to allow the negative pressure in FIG. 14D and the positive pressure in FIG. 14F to be applied). The ports 2302 and 2306 may form a chamber that is separate and isolated from the chamber above the target 1404 (e.g., the inner chamber 1402 as illustrated in FIG. 14A may be separate and isolated from the chamber that forms the seal 1406 in FIG. 14B). In one embodiment, an object (e.g., an object 401 of FIG. 4) on the cut-away view 2300 contacts the biological external tissue 302 within the chamber above the target 1404 and pushes blood within the biological external tissue 302 surrounding the target 1404 outside the chamber. Also illustrated in FIG. 23 is a number of energy panel 2312. Each energy panel 2312 may be connected to one or more energy sources (e.g., energy sources 503a-c as illustrated in FIG. 5).

FIG. 24 is a three-dimensional view of a device 2400 having an inner chamber 2404 and an outer portion 2402 to treat biological external tissue 312 according to one embodiment. Portions of FIG. 24 have been previously described in detail in conjunction with FIG. 16. In addition, the inner chamber 2404 in FIG. 24 may completely cover the target 1404 as illustrated in FIG. 24. Furthermore, the inner chamber 2404 may be completely isolated (e.g., isolated pressure wise) from the outer portion 2402. In addition, a camera and/or video recording device (not shown) having a lens may be connected to the device 2400 so that a user can view the biological external tissue within the inner chamber 2404. In another embodiment, the inner portion may be manually aligned (e.g., through physical marking of the biological external tissue 302 around the target 1404, and/or by replacing a removable and adjustable size fitting (not shown) for the inner chamber 2404 prior to application of the device 2400 onto the biological external tissue, etc.).

Various sensor(s) 2406 may be installed on the device 2400 in one embodiment. Various sensor(s) 2406 may include skin color sensors, temperature sensors, motion sensors, vapor pressure sensors (e.g., to sense negative and/or positive pressure within a chamber), material sensors (e.g., to sense the presence of water or other material within the chamber), temperature sensors, capacitance sensors, and a variety of other types of sensors and/or electronics described in FIGS. 1-13. Furthermore, the device 2400 may include a vacuum 2408 that generates a negative pressure within the outer portion 2402 to seal (e.g., the seal 1406 as illustrated in FIG. 14) the device 2400 to the biological external tissue 302.

The device 2400 in FIG. 24 may include one or more energy source(s) 2412. The energy source(s) 2412 may deliver energy 1414 as described in FIG. 14E. In another embodiment, energy source(s) 2412 may be energy sources described in FIGS. 3-13 (e.g., energy source 503a-c as illustrated in FIG. 5). The device 2400 may also include a liquid/negative pressure applicator 2410 to apply liquid/negative pressure to the inner chamber 2404. In one embodiment, the liquid/negative pressure applicator 2410 applies the material 1408 to the biological external tissue 302 within the inner chamber 2404. In another embodiment, the liquid/negative pressure applicator 2410 applies a negative pressure to the biological external tissue 302 within the inner chamber 2404 to bring the target 1404 and surrounding biological external tissue 302 into the inner chamber 2404.

It should be noted that the various embodiments having sensors, and electronics described herein may be performed within hardware circuitry as well as in software. Specifically, it should be noted that an electrical architecture for a handheld device as described in FIG. 13 can be implemented with one or more semiconductor devices including circuitry such as logic circuitry to perform its various functions as described above, in addition to being implemented in software. In some embodiments, hardware circuitry may provide speed and performance advantages over software implementations of the device 1301 shown in FIG. 13. In other embodiments, software implementations may be preferred. In one embodiment, the sensors 1305 in FIG. 13 may be designed using an electrical skin contact sensor circuit, a pressure sensor circuit, a skin temperature circuit, and/or any combination of these sensor circuits, and may be built with semiconductor circuitry (e.g., logic circuitry such as CMOS based circuitry). A semiconductor chip may implement the functions (e.g., as described in FIGS. 2 thru FIG. 24) described within the various embodiments using logic gates, transistors, and hardware logic circuitry associated with implementing the various embodiments disclosed herein.

The subject invention has been described with reference to numerous details set forth herein and the accompanying drawings. This description and accompanying drawings are illustrative of the invention and are not to be construed as limiting the invention. It will be evident that various modifications may be made thereto without departing from the broader spirit and scope of the invention as set forth in the following claims.

What is claimed:

1. A method to treat a target, comprising:
applying a device to a biological external tissue, the device having a peripheral border that includes an outer portion that is brought into contact with a first portion of the biological external tissue;
applying a first negative pressure inside the outer portion of the device through a conduit coupled to the outer portion of the device, the device having an inner chamber which is surrounded, at the peripheral border, by the outer portion, and wherein the inner chamber occupies a space above a second portion of the biological external tissue and wherein the first portion of the biological external tissue surrounds the second portion of the biological external tissue;
furnishing a liquid to the second portion of the biological external tissue inside the inner chamber of the device;
applying a second negative pressure, through an opening in the inner chamber of the device, inside the inner chamber equal to or lower than a vapor pressure of the liquid while the biological external tissue is coated with the liquid;
applying an energy to the second portion of the biological external tissue inside the inner chamber; and causing the liquid to evaporate at least in part via the second negative pressure.

2. The method of claim 1, wherein the first negative pressure inside the outer portion is applied before applying the second negative pressure such that the first negative pressure acts as a peripheral vacuum seal.

3. The method of claim 2, further comprising:
displaying at least one measurement of a sensor on the device;
providing power to the device; and
sequentially generating a positive pressure and a negative pressure inside the inner chamber through a pressure source connected to the device through a cable element.

4. The method of claim 2, further comprising reducing pressure of the inner chamber to a first pressure that is below atmospheric pressure to bring at least some of the biological external tissue into the inner chamber.

5. The method of claim 2, further comprising preventing the biological external tissue that is outside the device from stretching.

6. The method of claim 5, further comprising:
monitoring the biological external tissue during treatment; and
releasing the vacuum seal to allow the device to be removed before the biological external tissue is damaged.

7. The method of claim 1, wherein the causing the liquid to evaporate is performed through vaporization during application of the energy to treat the target.

8. The method of claim 7, wherein the energy originates from a source that is not exposed to any pressure inside the inner chamber.

9. The method of claim 7, wherein the energy is at least one of an incoherent light, a coherent light, a radio frequency, or an ultrasound.

10. The method of claim 7, further comprising automatically regulating a power level of the energy.

11. The method of claim 1, further comprising:
measuring a blood concentration in the biological external tissue during treatment; and
applying an electrical current to the target before the blood concentration in the biological external tissue returns to at least a normal state or higher concentration than normal.

12. The method of claim 1, further comprising measuring a color of the biological external tissue.

13. The method of claim 1, further comprising measuring a temperature of the biological external tissue.

14. The method of claim 1, further comprising: pushing away blood inside the biological external tissue.

15. A method of treating an area of biological external tissue having a target using a device, comprising:
coating a liquid on a second portion of a biological external tissue which includes the target and which is surrounded by a first portion of the biological external tissue;
applying a device to the biological external tissue, the device having a peripheral border that includes an outer portion that is brought into contact with the first portion of the biological external tissue;
applying a first negative pressure inside the outer portion of the device through a conduit coupled to the outer portion of the device, the device having an inner chamber which is surrounded, at the peripheral border, by the outer portion, and wherein the inner chamber occupies a space above the second portion of the biological external tissue;
applying a first positive pressure inside the inner chamber of the device on the second portion of the biological external tissue;
applying a second negative pressure, through an opening in the inner chamber of the device, inside the inner chamber to bring the second portion of the biological external tissue closer to the device;
forming a pressure equal to or lower than a vapor pressure of the liquid while the second portion of the biological external tissue is coated with the liquid;
causing the liquid to evaporate at least in part via the second negative pressure;
measuring a blood concentration in the biological external tissue;
applying an energy to the target before the blood concentration in the second portion of the biological external tissue returns to at least a normal state; and
applying a second positive pressure, through the opening in the inner chamber, inside the inner chamber on the second portion of the biological external tissue to allow the device to be released from the biological external tissue before the biological external tissue is damaged.

16. The method of claim 15, further comprising displaying at least one measurement of a sensor on the device.

17. The method of claim 16, wherein the device is a handheld device.

18. The method of claim 16, wherein the at least one sensor is chosen from a group comprising a skin color sensor, a temperature sensor, a motion sensor, a vapor pressure sensor, a material sensor, and a capacitance sensor.

19. The method of claim 15, further comprising causing the liquid to evaporate.

20. The method of claim 15, wherein the energy originates from a source that is not exposed to any pressure applied by the device.

21. The method of claim 15, wherein the first positive pressure pushes away blood inside the biological external tissue.

22. The method of claim 15, wherein the liquid is one of water and ethyl alcohol.

23. A method for treating a target with a device, the method comprising:
depositing a material on a second portion of a biological external tissue having the target and, wherein a first portion of the biological external tissue surrounds the second portion of the biological external tissue;
applying the device to the first portion and second portion of the biological external tissue, the device having a peripheral border that includes an outer portion that is brought into contact with the first portion;
applying a first negative pressure inside the outer portion of the device through a conduit coupled to the outer portion of the device, the device having an inner chamber which is surrounded, at the peripheral borders, by the outer portion, and wherein the inner chamber occupies a space above the second portion of the biological external tissue;
applying a second negative pressure, through an opening in the inner chamber, on the second portion of the biological external tissue to bring the second portion of the biological external tissue into contact with a protruding object of the device that is above the second portion of the biological external tissue while the second portion of the biological external tissue is coated with the material;
measuring a blood concentration in the biological external tissue;
applying an energy to the second portion of the biological external tissue before the blood concentration in the second portion of the biological external tissue returns to at least a normal state, and causing the material to evaporate at least in part via the second negative pressure; and
applying a positive pressure inside the inner chamber on the second portion of the biological external tissue to allow the device to be released from the biological external tissue before the biological external tissue is damaged.

24. The method of claim 23, further comprising applying a positive pressure on the area and then removing the device from the area.

25. The method of claim 23, wherein the material is applied during application of the energy and wherein the material provides evaporative cooling.

26. A system to treat biological external tissue using a device, comprising:
means for applying a first negative pressure through a conduit of the device, inside an outer portion of the device wherein the device has a peripheral border that includes the outer portion which is brought into contact with a first portion of the biological external tissue, and wherein the device includes an inner chamber which is surrounded, at the peripheral border, by the outer potion, and wherein the inner chamber occupies a space above a second portion of the biological external tissue that is surrounded by the first portion of the biological external tissue;
means for reducing temperature of the second portion of the biological external tissue having a target by depositing a material on the second portion of the biological external tissue;
means for applying a second negative pressure, through an opening in the inner chamber, inside the inner chamber of the device equal to or lower than a vapor pressure of the material while the second portion of the biological external tissue is coated with the material to cause the material to evaporate at least in part via the second negative pressure and to bring the second portion of the biological external tissue into the inner chamber of the device; and means for applying an energy to the target before the blood concentration in the area returns to at least a normal state.

27. The system of claim 26, further comprising means for applying a positive pressure to allow the device to be released before the biological external tissue is damaged.

28. The system of claim 26, wherein the material has a vapor pressure below atmospheric pressure.

* * * * *